United States Patent
Memmolo et al.

(10) Patent No.: US 9,433,438 B2
(45) Date of Patent: Sep. 6, 2016

(54) LOCKING MEMBER FOR A BONE FIXATION DEVICE

(71) Applicant: DePuy Synthes Products, Inc., Raynham, MA (US)

(72) Inventors: Marcello Memmolo, Oberdorf (CH); Kurtis Wheeler, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 282 days.

(21) Appl. No.: 14/077,366

(22) Filed: Nov. 12, 2013

(65) Prior Publication Data

US 2014/0135852 A1    May 15, 2014

Related U.S. Application Data

(60) Provisional application No. 61/726,797, filed on Nov. 15, 2012.

(51) Int. Cl.
   *A61B 17/68*    (2006.01)

(52) U.S. Cl.
   CPC .................. *A61B 17/688* (2013.01)

(58) Field of Classification Search
   CPC .. A61B 17/68; A61B 17/683; A61B 17/685; A61B 17/688; A61B 17/80; A61B 17/8004; A61B 17/8009; A61B 17/8019; A61B 17/8028; A61B 17/8061; A61B 17/8076; A61B 17/808; A61B 17/809; A61B 17/82; A61B 17/823; A61B 2017/681; F16B 21/073; Y10T 24/1498; Y10T 403/32434; Y10T 403/4628; Y10T 403/4674; Y10T 403/4682; Y10T 403/4688
   See application file for complete search history.

(56) References Cited

U.S. PATENT DOCUMENTS

| | | | | |
|---|---|---|---|---|
| 1,831,613 A | * | 11/1931 | Symons | E04G 25/06 248/354.6 |
| 3,545,387 A | * | 12/1970 | Giambalvo | A47B 57/26 108/101 |
| 4,802,477 A | * | 2/1989 | Gabbay | A61B 17/0643 606/74 |
| 4,828,444 A | * | 5/1989 | Oshida | F16B 37/043 411/437 |
| 4,934,889 A | * | 6/1990 | Kurosaki | F16B 37/0842 411/267 |

(Continued)

FOREIGN PATENT DOCUMENTS

| | | |
|---|---|---|
| JP | 5220174 | 8/1993 |
| WO | WO 2012/114360 A1 | 8/2012 |

OTHER PUBLICATIONS

U.S. Appl. No. 61/616,555, filed Mar. 28, 2012, Knueppel.

*Primary Examiner* — Christian Sevilla
*Assistant Examiner* — Eric S Gibson
(74) *Attorney, Agent, or Firm* — Baker & Hostetler LLP

(57) ABSTRACT

A locking member for a bone fixation device can include a locking body that defines an outer surface, an opposed bone contacting surface, and a slot that extends from the bone contacting surface to the outer surface. The locking member can further include at least one locking tooth that extends into the slot and a biasing member that extends into the slot and defines an abutment surface that faces the at least one locking tooth. The slot can be configured to receive a toothed member along an insertion direction and the biasing member can be configured to bias the toothed member toward the at least one locking tooth such that at least one tooth of the toothed member engages the at least one locking tooth of the locking member so as to prevent the toothed member from translating through the slot along a direction that is opposite the insertion direction.

34 Claims, 14 Drawing Sheets

(56) References Cited

U.S. PATENT DOCUMENTS

| | | | |
|---|---|---|---|
| 5,111,557 A * | 5/1992 | Baum | A44B 17/007 24/297 |
| 5,350,399 A * | 9/1994 | Erlebacher | A61B 17/0057 128/899 |
| 5,707,373 A | 1/1998 | Sevrain et al. | |
| 5,800,436 A | 9/1998 | Lerch | |
| 6,022,351 A * | 2/2000 | Bremer | A61B 17/688 606/324 |
| 6,068,631 A * | 5/2000 | Lerch | A61B 17/688 606/301 |
| 6,155,762 A * | 12/2000 | Courtin | F16B 37/0842 411/433 |
| 6,197,037 B1 | 3/2001 | Hair | |
| 6,258,091 B1 | 7/2001 | Sevrain et al. | |
| 6,270,500 B1 | 8/2001 | Lerch | |
| 6,328,743 B2 | 12/2001 | Lerch | |
| 6,338,602 B1 * | 1/2002 | Gombert | F16B 21/073 411/339 |
| 6,379,363 B1 * | 4/2002 | Herrington | A61B 17/688 606/104 |
| 6,485,493 B1 * | 11/2002 | Bremer | A61B 17/688 606/215 |
| 6,685,707 B2 * | 2/2004 | Roman | A61B 17/688 606/213 |
| 6,726,688 B2 | 4/2004 | Lerch | |
| 6,755,834 B2 * | 6/2004 | Amis | A61B 17/688 606/104 |
| 6,921,401 B2 * | 7/2005 | Lerch | A61B 17/688 606/232 |
| 7,322,784 B2 * | 1/2008 | Castro | F16B 37/0842 411/433 |
| 7,674,280 B2 | 3/2010 | Nesper et al. | |
| 8,241,342 B2 * | 8/2012 | Kirschman | A61B 17/688 606/324 |
| 8,920,095 B2 * | 12/2014 | Baugh, Sr. | F16B 21/073 411/512 |
| 9,034,020 B2 * | 5/2015 | Knopfle | A61B 17/688 606/282 |
| 9,149,297 B2 * | 10/2015 | Kirschman | A61B 17/688 |
| 2002/0016593 A1 * | 2/2002 | Hearn | A61B 17/688 606/916 |
| 2002/0062128 A1 * | 5/2002 | Amis | A61B 17/688 606/916 |
| 2002/0156475 A1 * | 10/2002 | Lerch | A61B 17/688 606/70 |
| 2002/0169455 A1 * | 11/2002 | Bannerman | A61B 17/688 606/99 |
| 2003/0036760 A1 * | 2/2003 | Yeh | A61B 17/688 606/71 |
| 2003/0176890 A1 * | 9/2003 | Buckman | A61B 17/08 606/213 |
| 2003/0229349 A1 * | 12/2003 | Wellisz | A61B 17/688 606/70 |
| 2004/0034352 A1 * | 2/2004 | Needham | A61B 17/8869 606/86 R |
| 2004/0034375 A1 * | 2/2004 | Ruiz | A61B 17/688 606/51 |
| 2004/0102779 A1 * | 5/2004 | Nesper | A61B 17/688 606/324 |
| 2004/0127908 A1 * | 7/2004 | Roman | A61B 17/688 606/916 |
| 2004/0140406 A1 * | 7/2004 | Kanie | F16B 5/0685 248/73 |
| 2005/0137608 A1 * | 6/2005 | Hearn | A61B 17/688 606/103 |
| 2006/0064110 A1 * | 3/2006 | Nesper | A61B 17/8869 606/105 |
| 2006/0122611 A1 * | 6/2006 | Morales | A61B 17/823 606/324 |
| 2008/0249532 A1 * | 10/2008 | Schoutens | A61B 17/688 606/60 |
| 2008/0275511 A1 * | 11/2008 | Weinacker | A61B 17/8869 606/324 |
| 2008/0281339 A1 * | 11/2008 | Kirschman | A61B 17/688 606/151 |
| 2009/0234357 A1 * | 9/2009 | Morales | A61B 17/8076 606/60 |
| 2009/0234358 A1 * | 9/2009 | Morales | A61B 17/8076 606/60 |
| 2010/0298828 A1 * | 11/2010 | Chico Roca | A61B 17/688 606/74 |
| 2010/0305619 A1 * | 12/2010 | Knopfle | A61B 17/688 606/282 |
| 2012/0165879 A1 * | 6/2012 | Khanna | A61B 17/688 606/286 |
| 2012/0290018 A1 * | 11/2012 | Kirschman | A61B 17/688 606/324 |
| 2013/0110181 A1 * | 5/2013 | Piotrowski | A61B 17/8869 606/324 |
| 2013/0190763 A1 | 7/2013 | Weisshaupt et al. | |
| 2013/0282011 A1 * | 10/2013 | Brogan | A61B 17/688 606/75 |
| 2014/0072386 A1 * | 3/2014 | Baugh, Sr. | F16B 19/00 411/337 |
| 2014/0135852 A1 * | 5/2014 | Memmolo | A61B 17/688 606/324 |
| 2014/0171944 A1 * | 6/2014 | Llas Vargas | A61B 17/8061 606/70 |
| 2014/0194907 A1 * | 7/2014 | Bonutti | A61B 17/8866 606/151 |
| 2015/0010372 A1 * | 1/2015 | Herrema | F16L 41/12 411/200 |
| 2015/0080975 A1 * | 3/2015 | Pleil | A61B 17/688 606/86 R |
| 2015/0252832 A1 * | 9/2015 | Le Grange | F16B 2/08 24/582.1 |
| 2015/0282840 A1 * | 10/2015 | Lemoine | A61B 17/8872 606/213 |

* cited by examiner

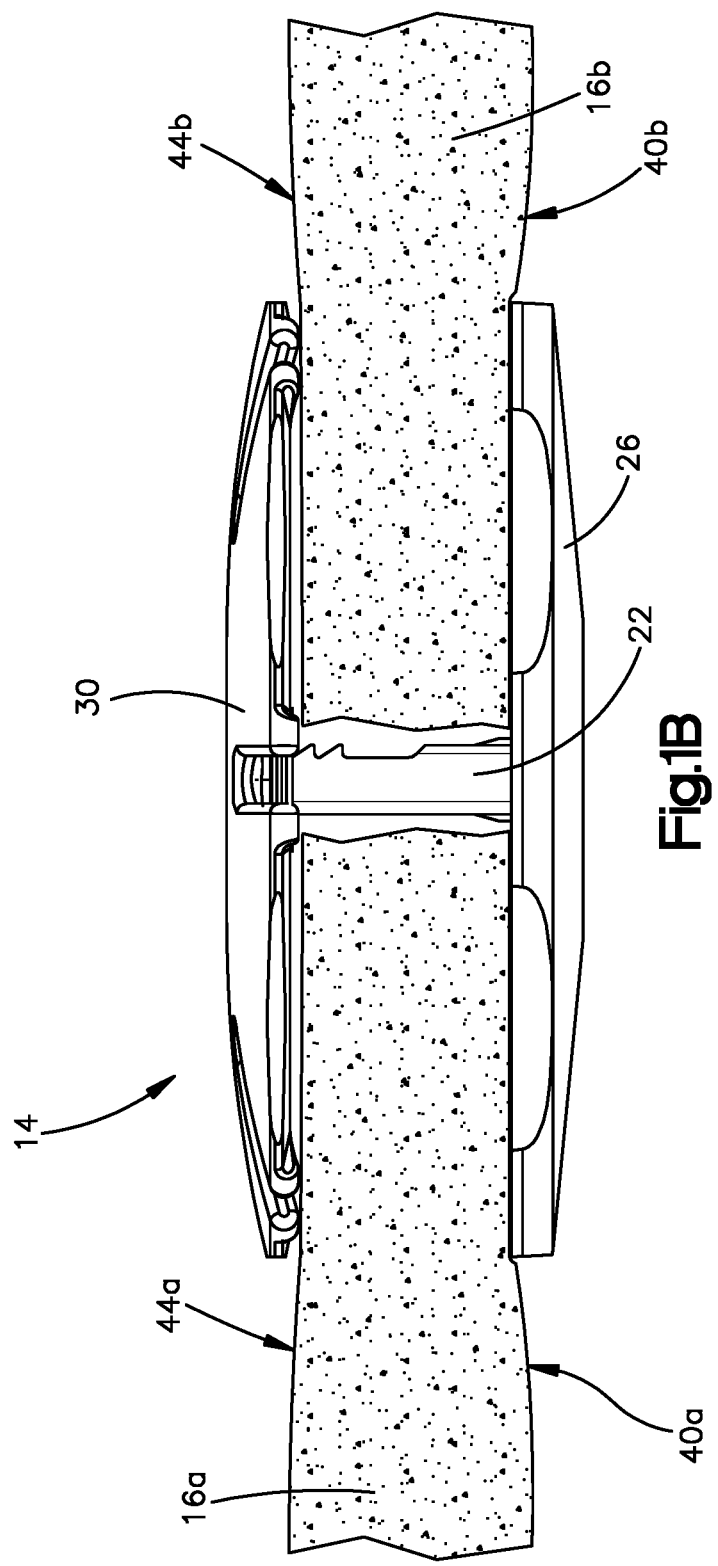

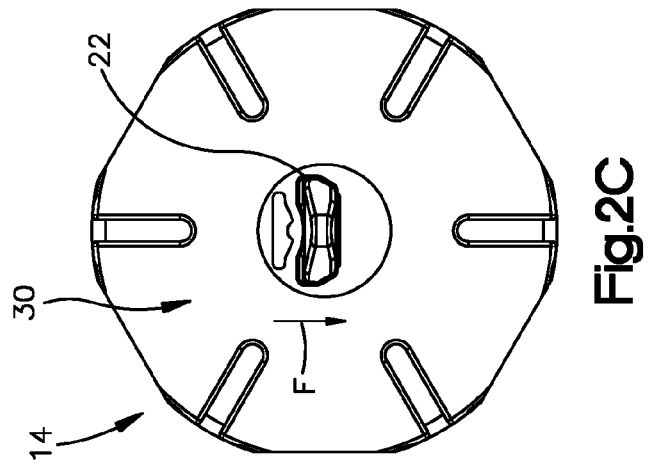
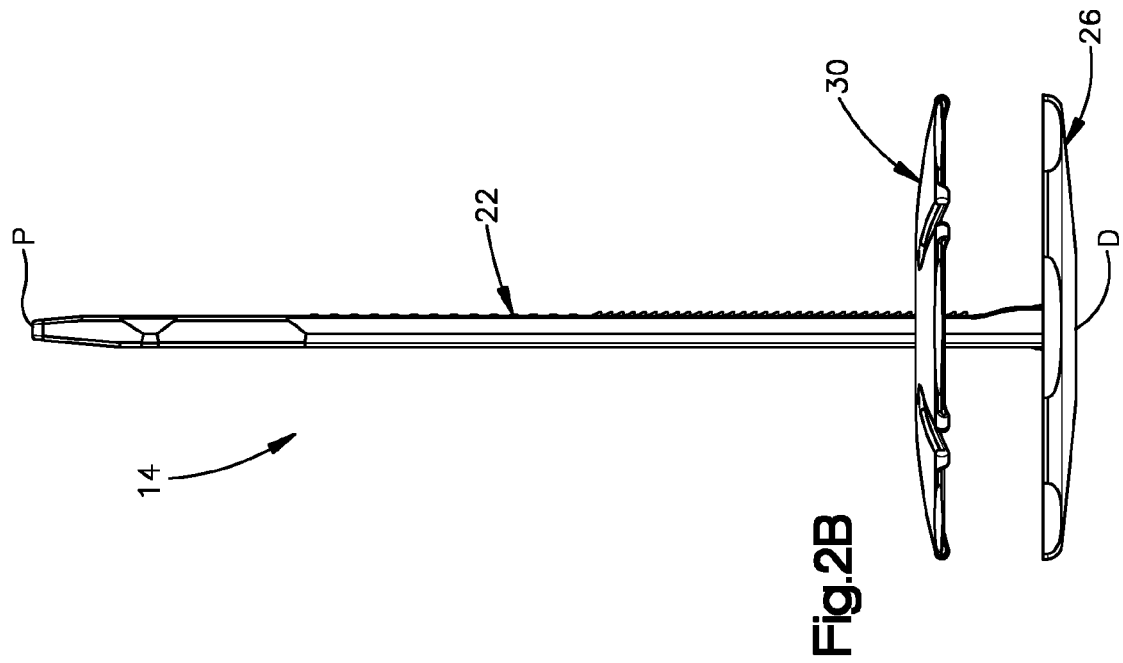

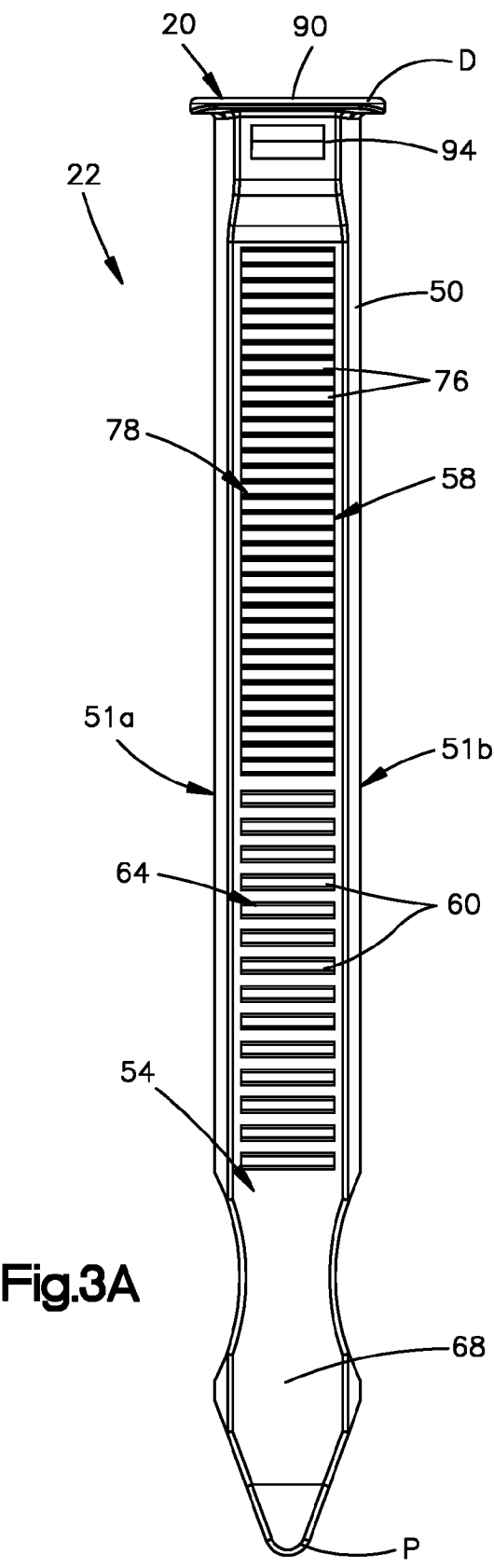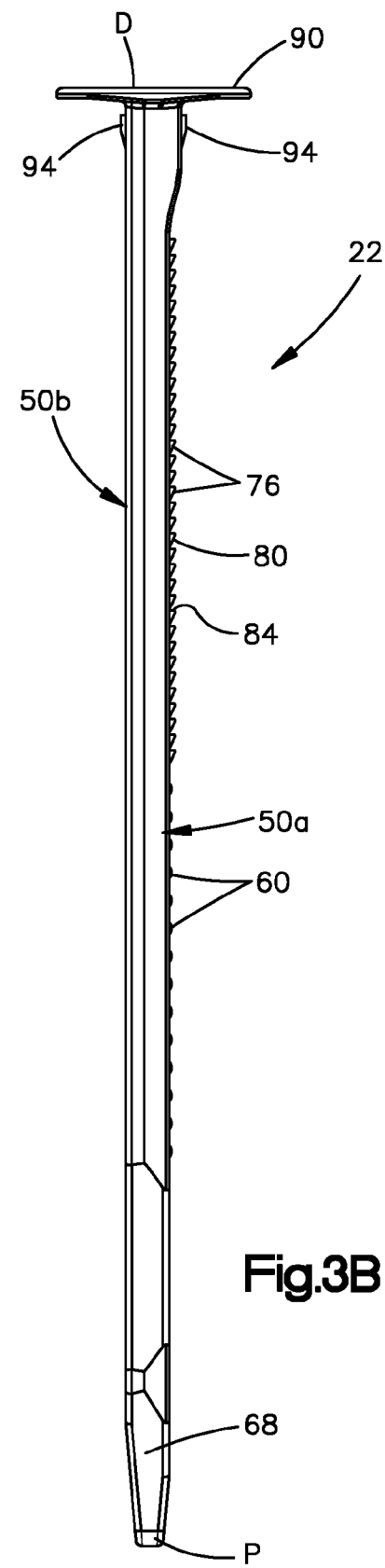

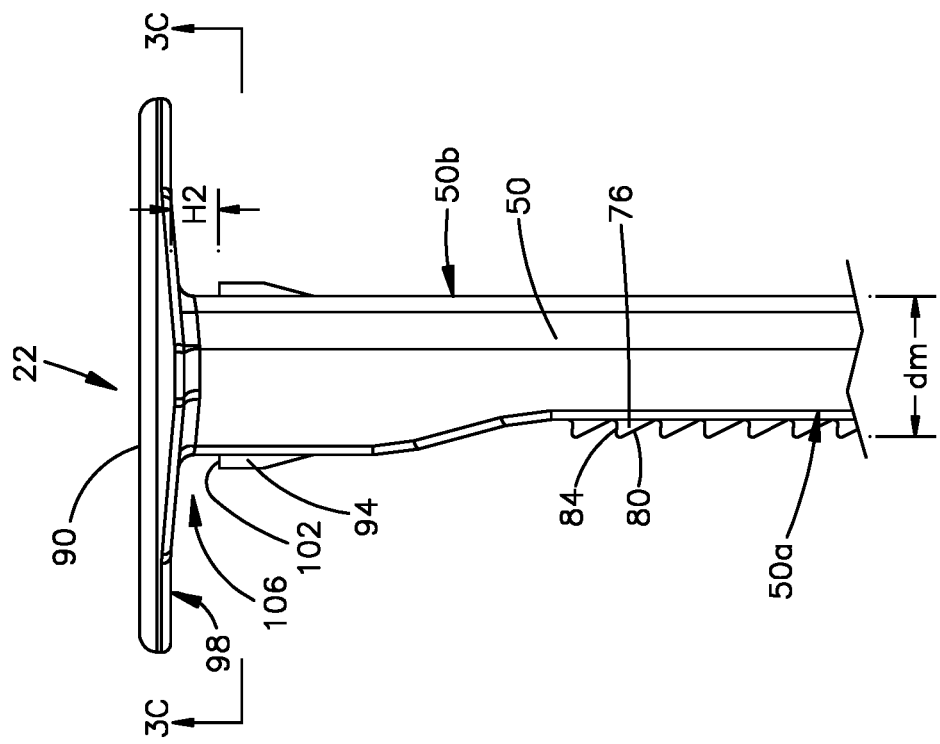
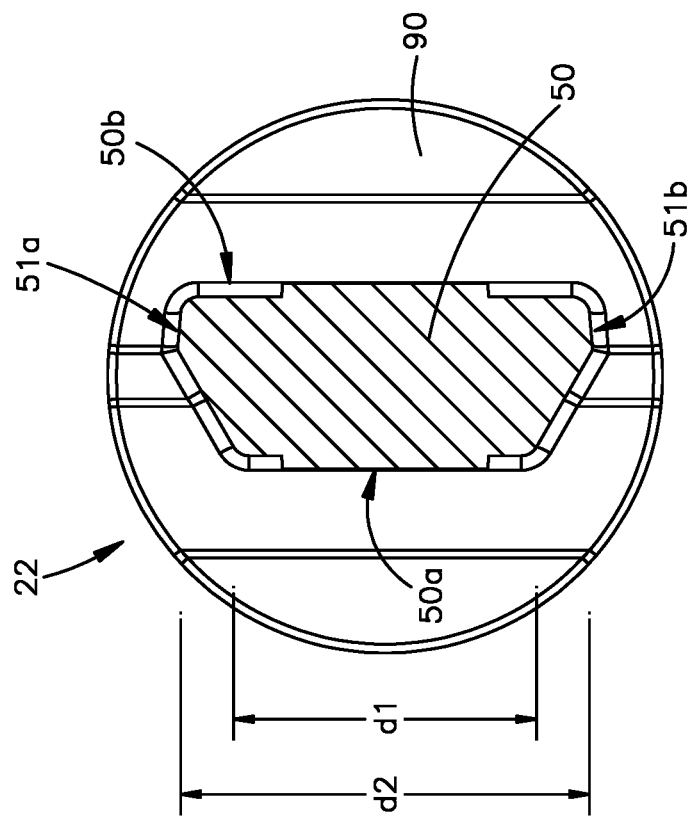
Fig.3D
Fig.3C

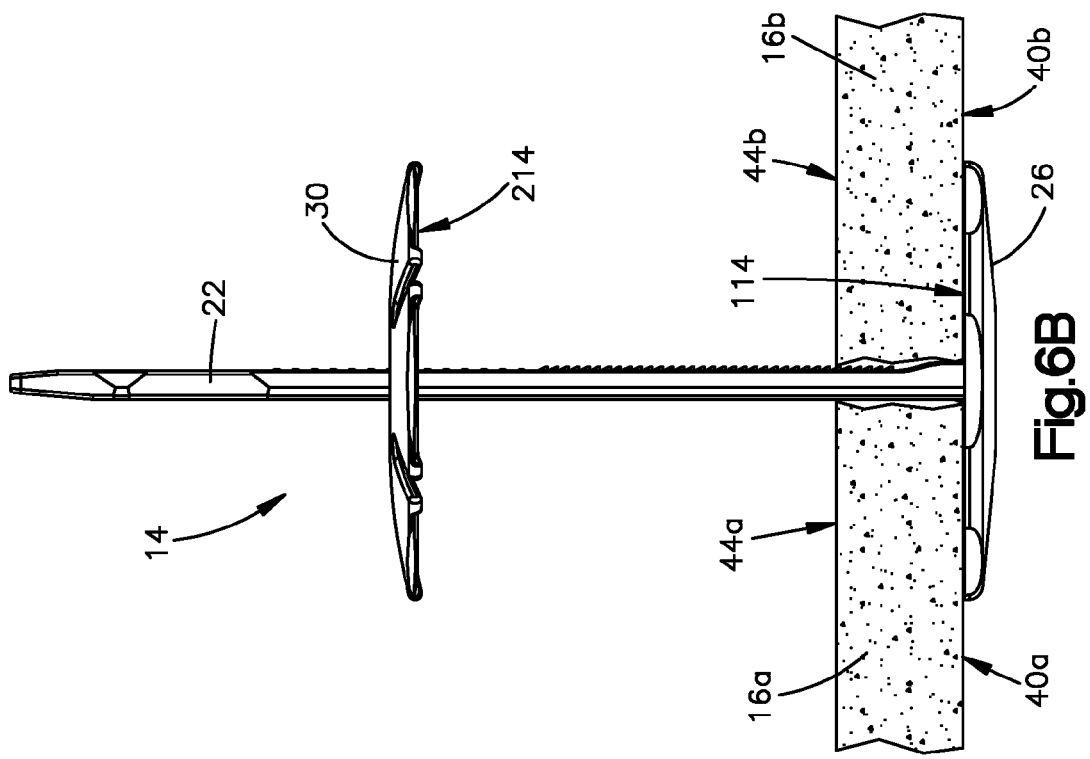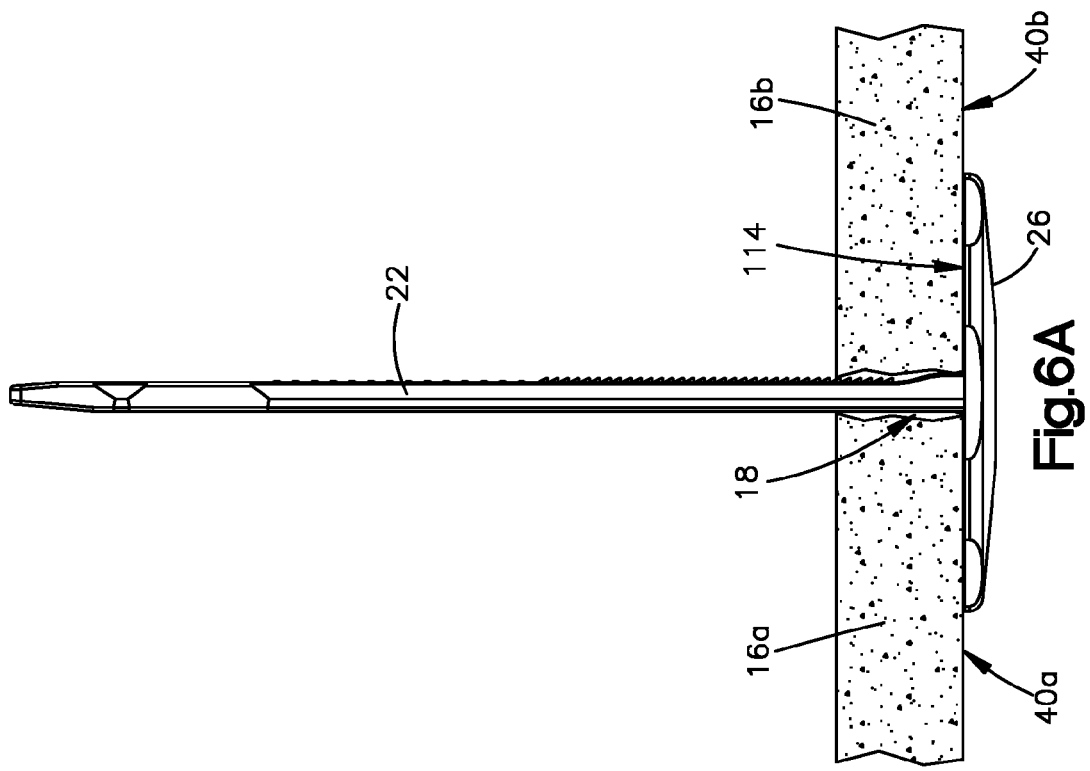

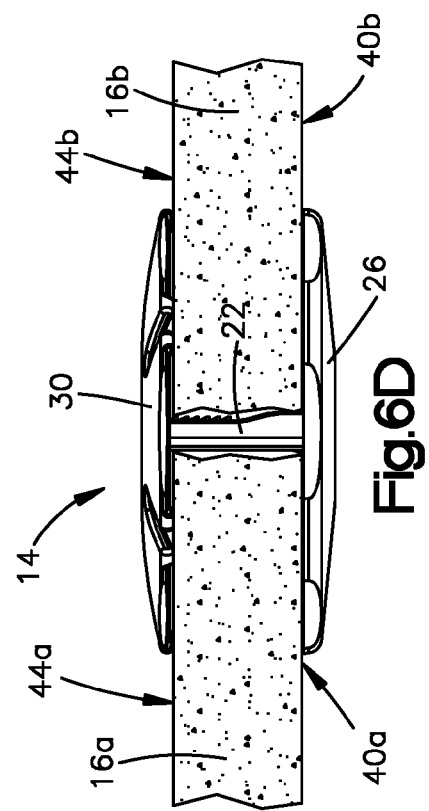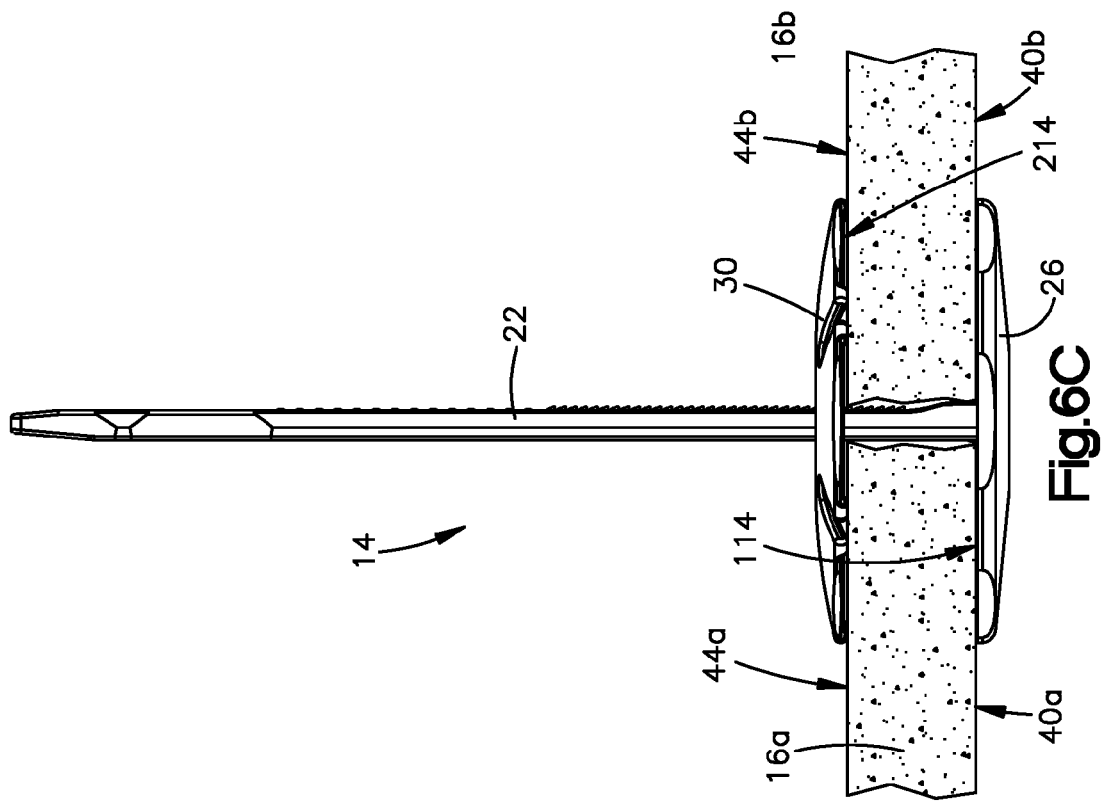

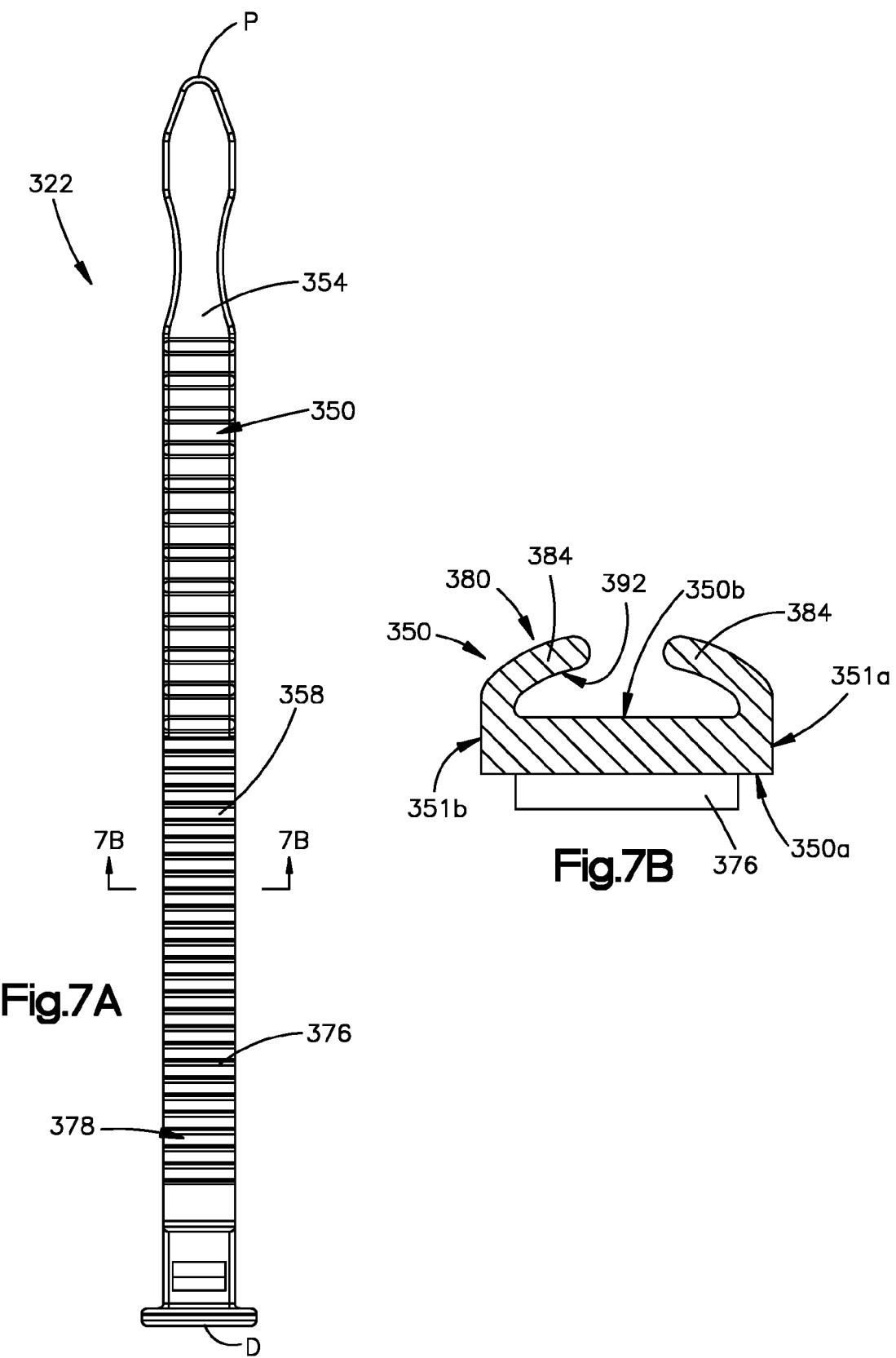

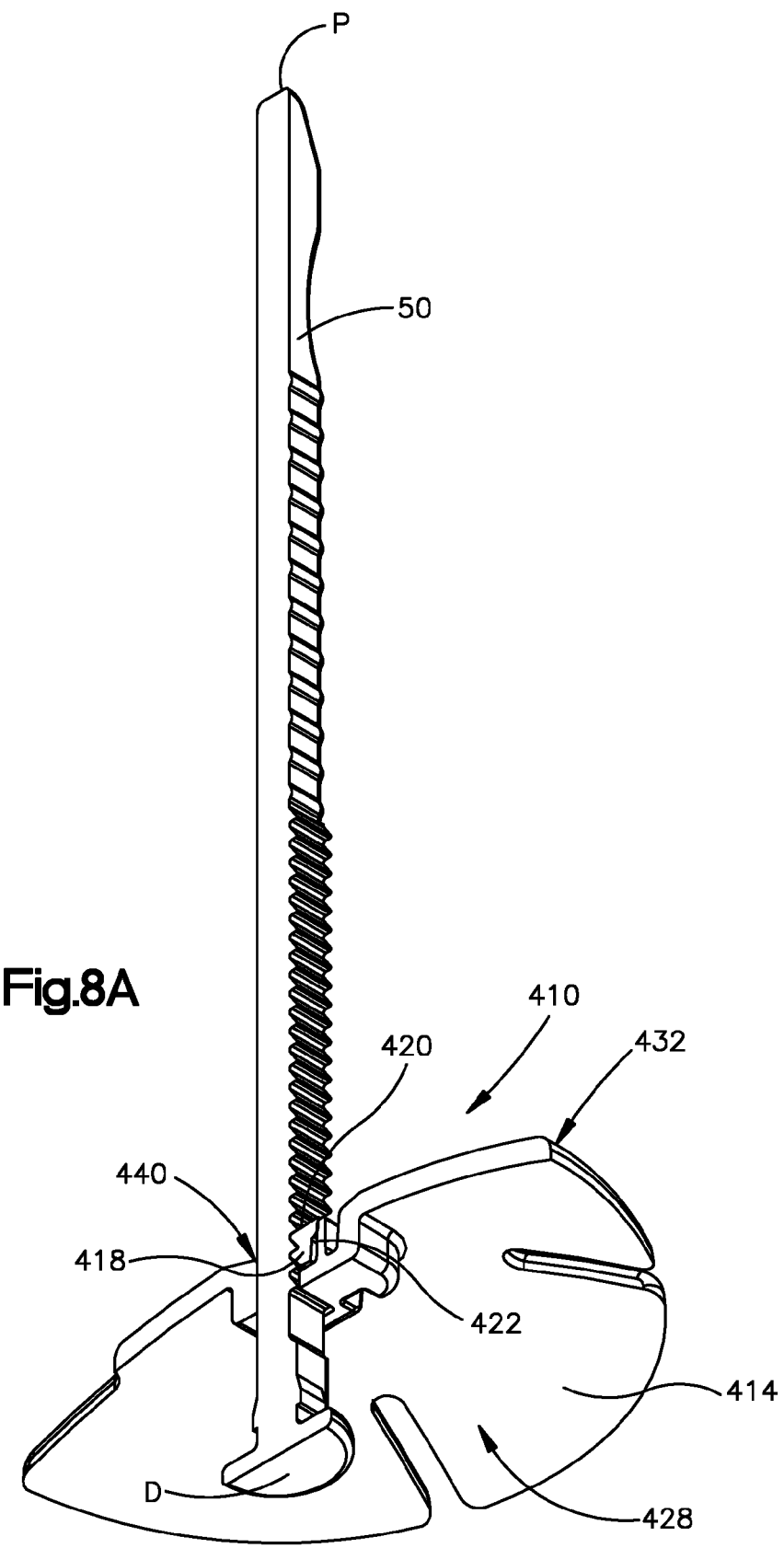

LOCKING MEMBER FOR A BONE FIXATION DEVICE

CROSS REFERENCE TO RELATED APPLICATIONS

This application claims priority to U.S. Provisional Application Ser. No. 61/726,797, filed Nov. 15, 2012, the contents of which are hereby incorporated by reference as if set forth in their entirety, herein.

BACKGROUND

There are various surgical procedures that require fixing soft tissue to bone or bone to bone to produce healing such as fixing a bone flap or bone implant to a patient's skull. For example, craniotomies are surgical procedures conducted to treat various brain injuries, including tumors and aneurysms. As part of a craniotomy procedure, the surgeon creates an opening in the skull. One technique is to drill several adjacent holes to define the periphery of the opening and then using a tool to cut between the holes. The surgeon can either remove an entire section of the skull, or cut a sufficient amount to bend the skull away to allow access to the brain or head region. The cut-out section is commonly referred to as a bone flap. In other cases, an implant may be required to replace a section of the skull that is missing. In both cases, the bone flap or implant must be secured or fixed to the surrounding skull after the surgical procedure is completed.

There are several existing devices for securing the bone flap or implant to the surrounding skull. Several of these devices include outer and inner disks that are connected by a stem, whereby the bone flap (or implant) and surrounding skull are sandwiched between the outer and inner disks. Typically during use, the outer disk is slidable along the stem toward the inner disk and is locked in place with a locking mechanism such as for example, a rivet, a frictional fit, or even a ratcheting member. While the ratcheting member has been the more desired locking mechanism, as a result of its use, the outer disk has a profile relative to the surrounding skull that tends to irritate the surrounding tissue and/or have undesirable cosmetic effects to the patient.

SUMMARY

A bone fixation device configured to affix adjacent anatomical structures relative to each other can include a stem, an inner member, and an outer member. The stem is elongate along a first direction and can include a first end and a second end that is spaced from the first end along the first direction. The stem can further include a plurality of teeth. The inner member is coupled to the first end of the stem and defines a first outer surface and a first inner surface. The first inner surface is configured to abut respective inner surfaces of the adjacent anatomical structures. The outer member is slidable along the stem from the second end and toward the inner member. The outer member can define a second outer surface and a second inner surface. The second inner surface is configured to abut respective outer surfaces of the adjacent anatomical structures. The outer member can include a stem receiving slot that extends from the second inner surface to the second outer surface, wherein the stem receiving slot is at least partially defined by a surface that includes at least one tooth and the outer member further includes a biasing member that extends into the stem receiving slot and is configured to bias the stem toward the surface such that at least one of the teeth of the stem engages the at least one tooth of the outer member when the stem is inserted through the stem receiving slot along an insertion direction so as to prevent the stem from translating through the stem receiving slot along a direction that is opposite the insertion direction.

In another embodiment, a locking member for a bone fixation device can include a locking body that defines an outer surface, an opposed inner bone contacting surface, and a slot that extends from the inner bone contacting surface to the outer surface. The locking member can further include at least one locking tooth that extends into the slot and a biasing member that extends into the slot and defines an abutment surface that faces the at least one locking tooth. The slot can be configured to receive a toothed member along an insertion direction and the biasing member can be configured to bias the toothed member toward the at least one locking tooth such that at least one tooth of the toothed member engages the at least one locking tooth of the locking member so as to prevent the toothed member from translating through the slot along a direction that is opposite the insertion direction.

BRIEF DESCRIPTION OF THE DRAWINGS

The foregoing summary, as well as the following detailed description, will be better understood when read in conjunction with the appended drawings. For the purposes of illustrating the present disclosure, there is shown in the drawings illustrative embodiments. It should be understood, however, that the application is not limited to the specific embodiments and methods disclosed, and reference is made to the claims for that purpose. In the drawings:

FIG. 1B is a cross-sectional view of one of the bone fixation devices of FIG. 1A affixing the bone flap to the surrounding skull portion;

FIG. 2B is a side elevation view of the bone fixation device shown in FIG. 2A;

FIG. 2C is a top plan view of the bone fixation device shown in FIG. 2A;

FIG. 3A is a front elevation view of the toothed stem shown in FIG. 2A, the toothed stem having a disk and a stem body that extends proximally from the disk;

FIG. 3B is a side elevation view of the toothed stem shown in FIG. 3A;

FIG. 3C is a cross-sectional view of the toothed stem shown in FIG. 3A through the line 3C-3C;

FIG. 3D is an enhanced side view of the distal end of the toothed stem shown in FIG. 3B;

FIG. 6A is a side elevation view of the first clamp member positioned such that an inner surface of the first clamp member is proximate to inner surfaces of respective first and second anatomical bodies and the toothed stem extending through a gap defined between the first and second anatomical bodies such that a portion of the toothed stem protrudes from and is external to the first and second anatomical bodies;

FIG. 6B is a side elevation view of the second clamp member positioned on the portion of the toothed stem that is external to the first and second anatomical bodies;

FIG. 6C is a side elevation view of the second clamp member positioned along the toothed stem such that an inner surface of the second clamp member is proximate to the outer surfaces of the respective first and second anatomical bodies;

FIG. 6D is a side elevation view of the first and second anatomical bodies trapped between the inner and outer disks and the toothed stem trimmed at a location proximate to the outer surface of the second clamp member;

FIG. 7A is a front plan view of a toothed stem in accordance with another embodiment;

FIG. 7B is a cross-sectional view of the toothed stem shown in FIG. 7A through the line 7B-7B, the toothed stem including a biasing member;

FIG. 8A is a perspective cross-sectional view of a locking member in accordance with another embodiment being translated along a toothed member, the locking member including a toothed body and a biasing member that is configured to bias the toothed body about a pivot.

DETAILED DESCRIPTION

Figure 1A:
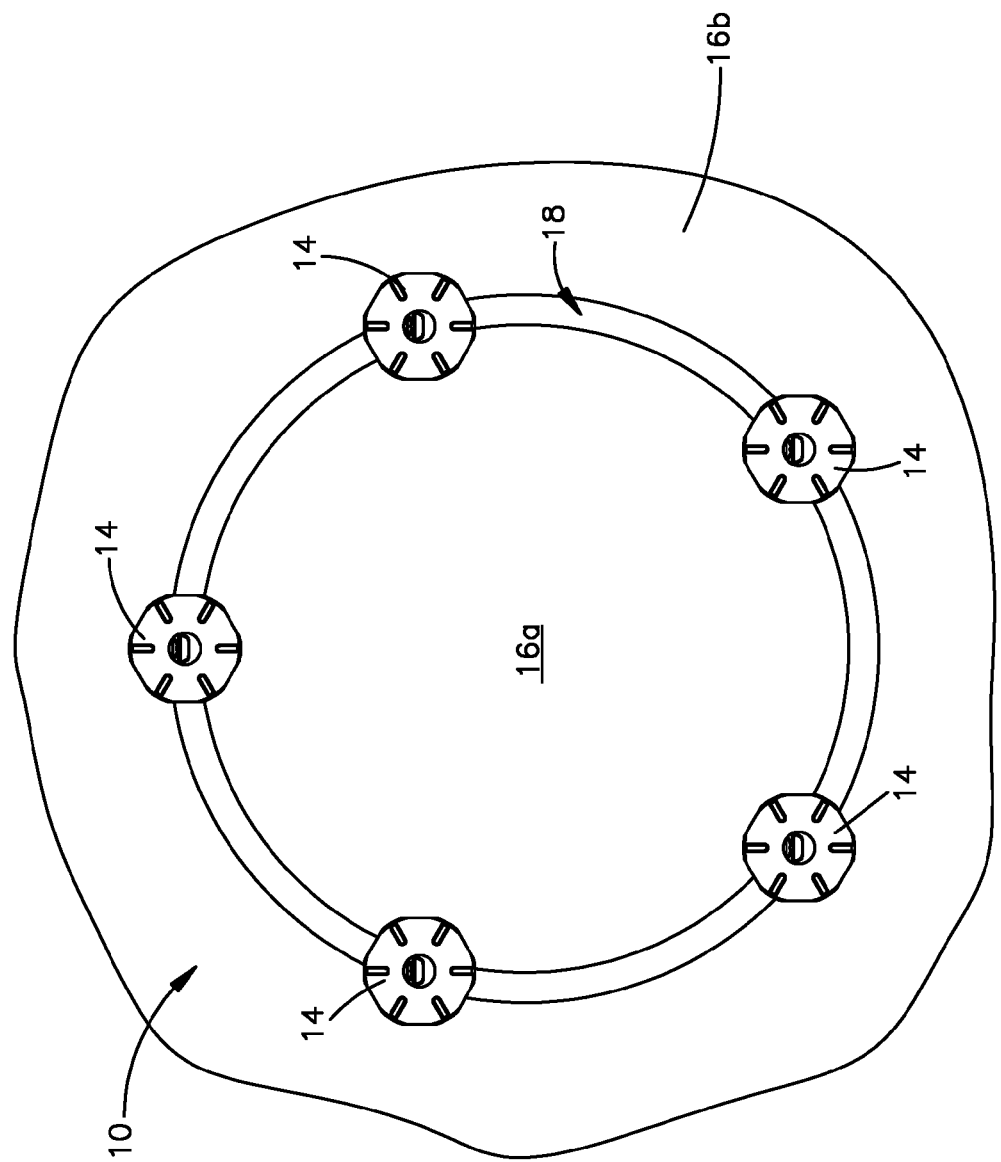
FIG. 1A is a perspective view of a plurality of bone fixation devices affixing a bone flap to a surrounding skull portion.
Figure 2A:
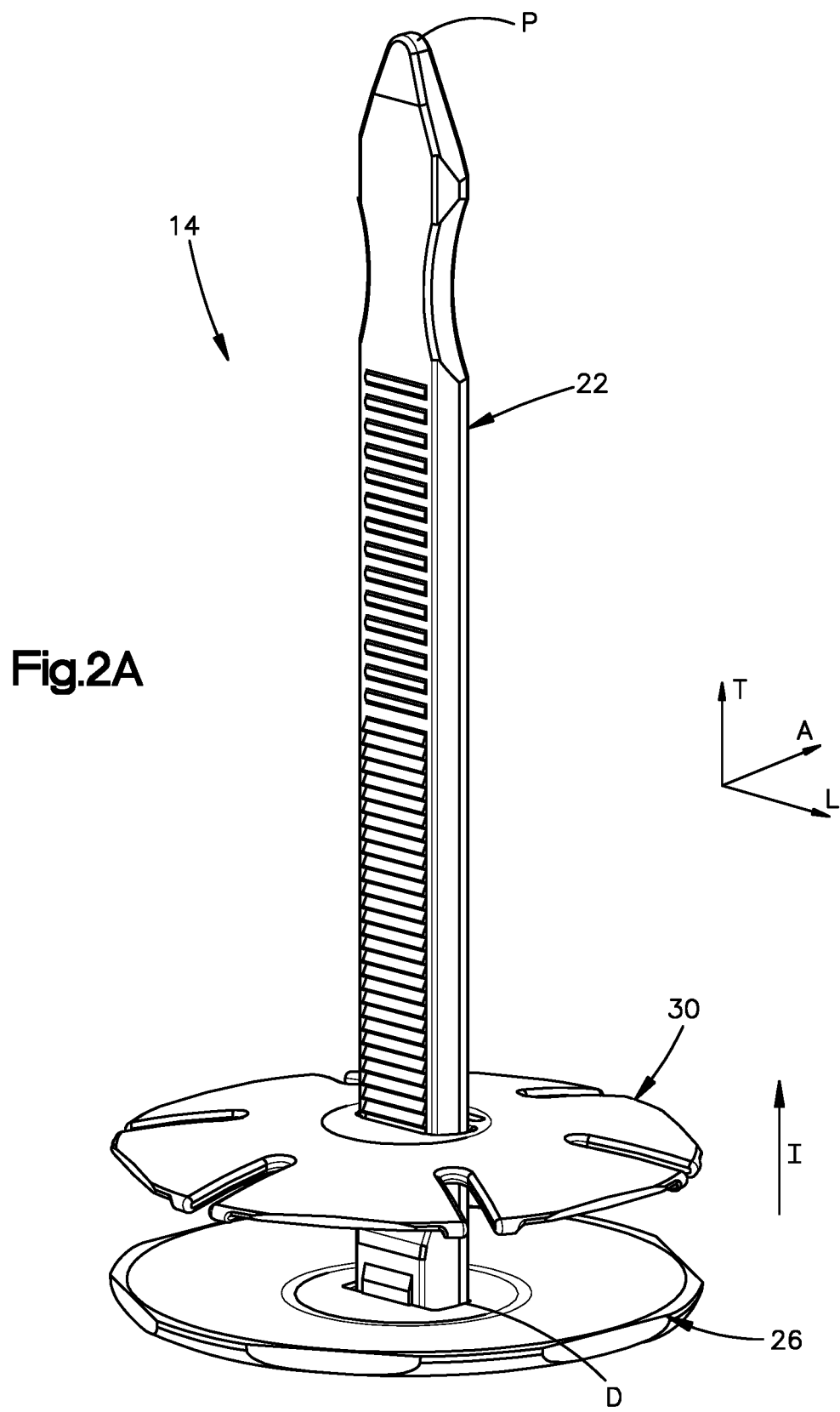
FIG. 2A is a perspective view of a bone fixation device in accordance with an embodiment, the bone fixation device having a toothed stem, a first clamp member coupled to a distal end of the toothed stem, and a second clamp member configured to translate along the toothed stem from a proximal end of the toothed stem that is opposite the distal end and toward the first clamp member.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical instrument. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Referring to FIGS. 1A and 1B, a bone fixation assembly 10 includes at least one bone fixation device 14 such as a plurality of bone fixation devices that are configured to affix or otherwise secure a first anatomical structure, such as an implant or a bone flap 16a to a second anatomical structure, such as a surrounding skull 16b that are separated by a bone gap 18 such as a fracture or cut. In the illustrated embodiment, five bone fixation devices 14 are used to affix the bone flap 16a to the surrounding skull 16b. It should be appreciated, however, that any number of bone fixation devices 14 can be used as desired.

As shown in FIGS. 1B and 2A-2C, the bone fixation device 14 can be substantially configured as a clamp, and extends horizontally along a longitudinal direction L and a lateral direction A, and vertically along a transverse direction T. The bone fixation device 14 includes a toothed member 20, illustrated as a toothed stem 22 that is elongate along the transverse direction T and defines a first or distal stem end D and a second or proximal stem end P that is spaced apart from the distal stem end D along the transverse direction T. The bone fixation device 14 can further include an inner or first clamp member 26 that extends from or is otherwise coupled to the distal stem end D and an outer or second clamp member 30 that is slidable along the toothed stem 22 from the proximal stem end P toward the first clamp member 26. It should be appreciated that the first and second clamp members 26 and 30 can be said to be first and second fixation members.

It should be appreciated, that while the longitudinal and lateral directions are described as extending horizontally and the transverse direction is described as extending vertically, that during use the plane in which the directions extend may change. For example, in use, the lateral direction may extend vertically, and the longitudinal direction and transverse direction may extend horizontally. Therefore it should be appreciated that the directional terms are for description purposes only and are not meant to be limiting. Moreover, it should be appreciated, that the transverse direction T, the longitudinal direction L, and the lateral direction A can be referred to as first, second, and third directions.

As shown in FIG. 1B, each bone fixation device 14 can be placed such that the first clamp member 26 is proximate to respective inner surfaces 40a and 40b of the bone flap 16a and the surrounding skull 16b. When positioned, the toothed stem 22 extends through the bone gap 18 and protrudes from the bone gap 18 such that a portion of the toothed stem 22 is external to the surrounding skull 16b. The second clamp member 30 can then be positioned over the proximal stem end P of the toothed stem 22 and translated along the toothed stem 22 toward the first clamp member 26. The second clamp member 30 is to be translated until the second clamp member 30 abuts respective outer surfaces 44a and 44b of the bone flap 16a and the surrounding skull 16b such that the bone flap 16a and the surrounding skull 16b are sandwiched between the first and second clamp members 26 and 30. It should be appreciated, however, that while the bone fixation devices 14 are illustrated as securing a bone flap 16a relative to the surrounding skull 16b, the bone fixation devices 14 can affix or otherwise secure any anatomical structures as desired, such as a sternum, for example.

The bone fixation device 14 including the toothed stem 22, the first clamp member 26, and the second clamp member 30 can be made from a biocompatible material such as PEEK or PEKK. The bone fixation device 14 can be molded as three separate components as illustrated. In such a case, the toothed stem 22 and the first clamp member 26 can be coupled together by the manufacturer or alternatively by a physician or physician's assistant prior to use. It should be appreciated, however, that the bone fixation device 14 can be molded as two components whereby the toothed stem 22 and the first clamp member 26 are molded as a single monolithic component that is to be later coupled to the second clamp member 30. Moreover, it should be appreciated that the bone fixation device 14 or at least one of the toothed stem 22, the first clamp member 26, and the second clamp member 30 can be made from a material other than PEEK or PEKK, such as a metal, for example.

Now in reference to FIGS. 3A-3D, the toothed stem 22 can include a stem body 50 that is separated into at least a first initiation region 54 that extends from the proximal stem end P toward the distal stem end D along a portion of the length of the toothed stem 22 (for instance, approximately ½ the length of the stem 22) and a second locking region 58 that extends between the first initiation region 54 and the distal stem end D. In accordance with the illustrated embodiment, the second locking region 58 extends from the first initiation region 54 to a location that is spaced from the distal stem end D. The stem body 50 defines opposed first and second surfaces 50a and 50b that are spaced from each other along the lateral direction A. As shown, the first and second surfaces 50a and 50b are connected together by a pair of side surfaces 51a and 51b. As shown, the first and second surfaces 50a and 50b are wider than the side surfaces 51a and 51b. It should be appreciated, however, that the first and second surfaces 50a and 50b can be narrower than the side surfaces 51a and 51b, as desired.

As shown in FIGS. 3A and 3B, the first initiation region 54 of the toothed stem 22 can include a plurality of small protrusions 60 that extend out from the first surface 50a of the stem body 50 and alternate with recessed regions 64 that are disposed between adjacent protrusions 60. The first initiation region 54 can further include a tapered end 68 that is proximal to the protrusions 60. The tapered end 68 can be substantially void of the protrusions 60 and the opposed side surfaces 51a and 51b at the tapered end can converge toward each other as they extend proximally toward the proximal stem end P. It should be appreciated, however, that the first initiation region 54 can be completely void of the protrusions 60, as desired and can be void of the tapered end 68 as desired.

As shown in FIG. 3A, the second locking region 58 of the toothed stem 22 can include a plurality of locking teeth 76 that extend out from the first surface 50a of the stem body 50 a distance greater than that of the protrusions 60 and are separated by recessed regions 78 that are disposed between adjacent locking teeth 76. It should be appreciated that that while the locking region 58 extends along a distal portion of the stem body in the illustrated embodiment, the locking region 58 can extend along any portion up to all of the stem body 50, as desired.

As shown in FIGS. 3A-3D, the locking teeth 76 extend from the stem body 50 along only the first surface 50a and are spaced from each other along the transverse direction T. Each locking tooth 76 is elongate along the longitudinal direction and is spaced from an adjacent tooth along the transverse direction T. Each tooth 76 defines a beveled leading or proximal edge 80 and a trailing or distal edge 84. The leading edges 80 extend from the first surface 50a at an angle such that the leading edges 80 are configured to cam over complementary beveled leading edges of complementary locking teeth of the second clamp member 30. The trailing edges 84 extend from the first surface 50a along the lateral direction and are substantially perpendicular to the first surface 50a such that the trailing edges 84 are configured to engage complementary trailing edges of the locking teeth of the second clamp member 30. It should be appreciated, however, that the locking teeth 76 can have other configurations as desired. For example, the trailing edges 84 can also extend from the first surface 50a at an angle so long as the trailing edges 84 can engage complementary trailing edges of the locking teeth of the second clamp member 30. Moreover, it should be appreciated, that the protrusions 60 and the locking teeth 76 can extend from both the first and second surfaces 50a and 50b or alternatively from at least one of the side surfaces 51a and 51b.

As shown in FIG. 3C, the stem body 50 can have a trapezoidal shape in cross-section. For example, in the illustrated embodiment the first surface 50a can have a longitudinal dimension $d_1$ that is less than a longitudinal dimension $d_2$ of the second surface 50b. The trapezoidal shape can help aid a user during assembly of the bone fixation device 14. That is, the second clamp member 30 will include a stem receiving slot that corresponds to the trapezoidal shape of the stem body 50. Therefore, the stem receiving slot of the second clamp member 30 will be able to receive the stem body 50 only when the stem body is in a correct orientation. Such a configuration will ensure that the second clamp member 30 is properly assembled with the toothed stem 22. It should be appreciated, however, that the stem body 50 can have any configuration as desired. For example, the stem body can have a rectangular shape in cross-section, as desired.

As shown in FIG. 3D, the toothed stem 22 can define a maximum distance $d_M$ from an exterior surface, such as the second surface 50b, of the stem body 50 to an outermost surface of at least one of the plurality of teeth 76 along a second direction that is substantially perpendicular to the first direction. It should be appreciated that the maximum distance $d_M$ should be measured at a tooth 76 that is configured to be received by a slot defined by the second clamp member 30. Moreover, it should be appreciated, that the maximum distance $d_M$ can be any distance as desired.

With continued reference to FIGS. 3A-3D, the toothed stem 22 can further include a first coupling member 90, illustrated as a disc, that extends from the distal stem end D and at least one second coupling member 94 that extends from the stem body 50 at a location spaced proximally from the distal stem end D. In the illustrated embodiment, the toothed stem 22 includes two second coupling members 94 that each extend from a respective one of the first and second surfaces 50a and 50b of the stem body 50. The first and second coupling members 90 and 94 are configured to mate with a portion of the first clamp member 26 to thereby couple the first clamp member 26 to the distal stem end D of the toothed stem 22. As shown in FIG. 3D, the first coupling member 90 defines a first trapping surface 98 and the second coupling members 94 each define respective second trapping surfaces 102 that face the first trapping surface 98. The first and second trapping surfaces 98 and 102 are spaced from each other along the transverse direction T such that respective gaps 106 are defined between each second trapping surface 102 and the first trapping surface 98. The gaps 106 are configured to receive a portion of the first clamp member 26 to thereby trap or otherwise couple the first clamp member 26 to the toothed stem 22. It should be appreciated, however, that while the first coupling member 90 is illustrated as a disc, the first coupling member 90 can have any desired configuration. For example, the first coupling member 90 can be block shaped. Moreover, it should be appreciated that the second coupling members 94 can extend from the side surfaces 51*a* and 51*b* as desired.

Figure 4A:
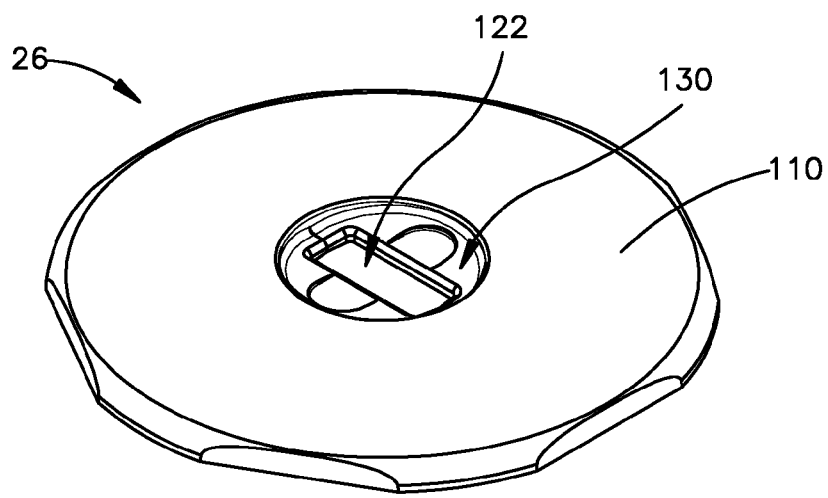
FIG. 4A is a perspective view of the first clamp member shown in FIG. 2A, the first clamp member defining a first stem receiving slot that is configured to receive the toothed stem so that the first clamp member can be coupled to the distal end of the toothed stem.
Figure 4B:
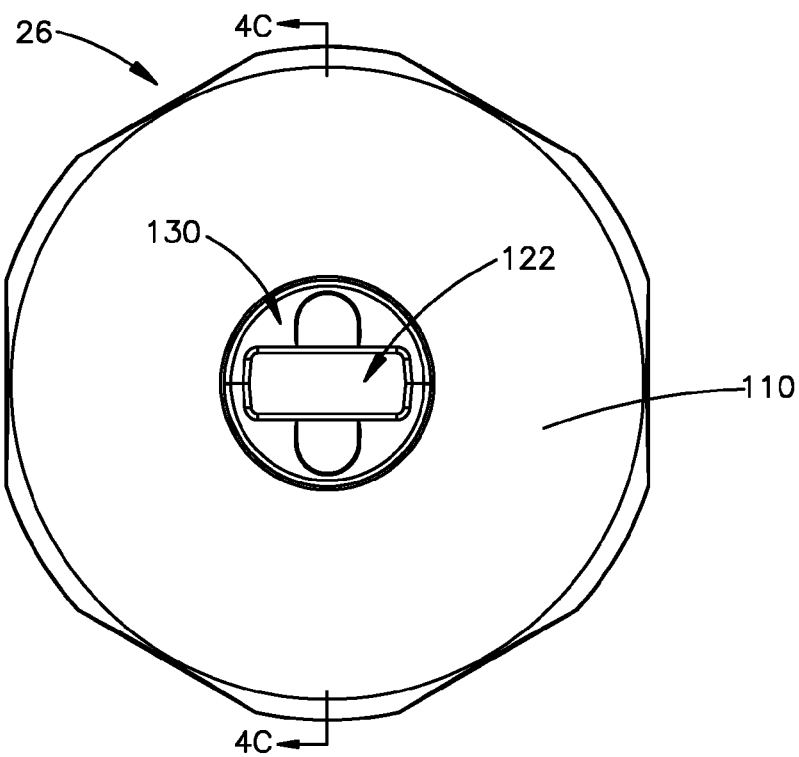
FIG. 4B is a top plan view of the first clamp member shown in FIG. 4A.
Figure 4C:
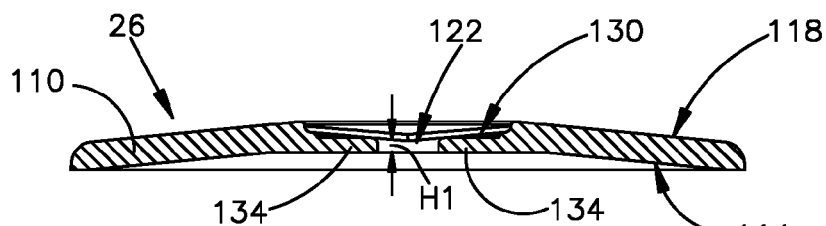
FIG. 4C is a cross-sectional view of the first clamp member shown in FIG. 4B through the line 4C-4C.

Now in reference to FIGS. 4A-4C, the first clamp member 26 is configured to be rigidly coupled to the distal stem end D of the toothed stem 22. The first clamp member 26 includes a first clamp or locking body 110 that is substantially cylindrical in shape when viewed from above and defines an inner or bone contacting surface 114 and an outer surface 118 that is opposite the inner surface 114 along the transverse direction T. As shown in FIG. 4C, the inner surface 114 is concave and the outer surface 118 is convex such that when the inner surface 114 contacts the inner surfaces 40*a* and 40*b* of the first and second anatomical structures 16*a* and 16*b*, the first body 110 flexes. It should be appreciated, however, that the first body 110 can have any configuration, as desired. For example, the first body 110 can be rectangular shaped and/or the inner and outer surfaces 114 and 118 can be substantially flat, as desired. Referring back to FIG. 2A, the first clamp member 26 is configured to be coupled to the distal stem end D of the toothed stem 22. In use the first clamp member 26 is configured to be positioned such that the inner surface 114 is proximate to the inner surfaces 40*a* and 40*b* of the first and second anatomical structures 16*a* and 16*b*. When the first clamp member 26 is moved into a clamping position the inner surface 114 contacts or otherwise abuts the inner surfaces 40*a* and 40*b* of the anatomical structures 16*a* and 16*b* and the first body 110 flexes outward.

As shown in FIGS. 4B and 4C the first clamp member 26 further defines a first stem receiving slot 122 that extends through the first body 110 from the inner surface 114 through to the outer surface 118 along the transverse direction T. The first stem receiving slot 122 is shaped to receive the stem body 50 along an insertion direction I such that the inner surface 114 faces the proximal stem end P. In the illustrated embodiment, the first stem receiving slot 122 is rectangular shaped in cross-section, though it should be appreciated that the stem receiving slot 122 can have any configuration as desired. For example, the first stem receiving slot 122 can be trapezoidal shaped in cross-section, as desired.

As shown in FIG. 4C, the first body 110 further defines a recess 130 that extends into the outer surface 118 and toward the inner surface 114. The recess 130 extends into but not completely through the first body 110 such that a pair of snap members 134 is defined. As shown, the snap members 134 are spaced from each other along the lateral direction A such that the stem receiving slot 122 is at least partially defined by the snap members 134. Therefore, the stem receiving slot 122 extends through the first body 110 from the inner surface 114 and into the recess 130.

The recess 130 is sized and shaped to receive the first coupling member 90 of the toothed stem 22 such that when the first coupling member 90 is received by the recess 130, the first coupling member 90 is substantially flush with the outer surface 118. In the illustrated embodiment, the recess is cylindrical in shape to correspond to the disc shape of the first coupling member 90. It should be appreciated, however, that the recess 130 can have any shape as desired and that the first coupling member 90 can protrude above the outer surface 118 or be recessed relative to the outer surface 118 as desired.

With continued reference to FIG. 4C, the snap members 134 are configured to be received by the gaps 106 of the toothed stem 22 when the first clamp member 26 is coupled to the toothed stem 22. As shown in FIG. 4C, the snap members 134 each have a transverse height $H_1$ that is substantially equal to a transverse height $H_2$ of the gaps 106 of the toothed stem 22. Therefore, when the snap members 134 are received by the gaps 106, the first clamp member 26 will be rigidly coupled to the distal stem end D of the toothed stem 22.

To couple the first clamp member 26 to the toothed stem 22, the proximal stem end P of the toothed stem 22 can be inserted into the first stem receiving slot 122 along a direction from the outer surface 118 toward the inner surface 114 such that the first clamp member 26 slides along the stem body 50 toward the first coupling member 90. The first clamp member 26 is to be moved toward the first coupling member 90 until the first coupling member 90 is received by the recess 130 and the snap members 134 have snapped into engagement with the gaps 106. Once the snap members 134 have engaged the gaps 106 and are trapped between the first and second trapping surfaces 98 and 102 of the first coupling member 90 and the second coupling members 94, respectively, the first clamp member 26 will be rigidly coupled to the distal stem end D of the toothed stem 22. The first clamp member 26 and the toothed stem 22 can together define a first locking member. It should be appreciated that the first clamp member 26 and the toothed stem 22 can be rigidly coupled together using any method or structure as desired. For example, the first clamp member 26 and the toothed stem can be welded together using for example ultrasound welding.

Figure 5A:
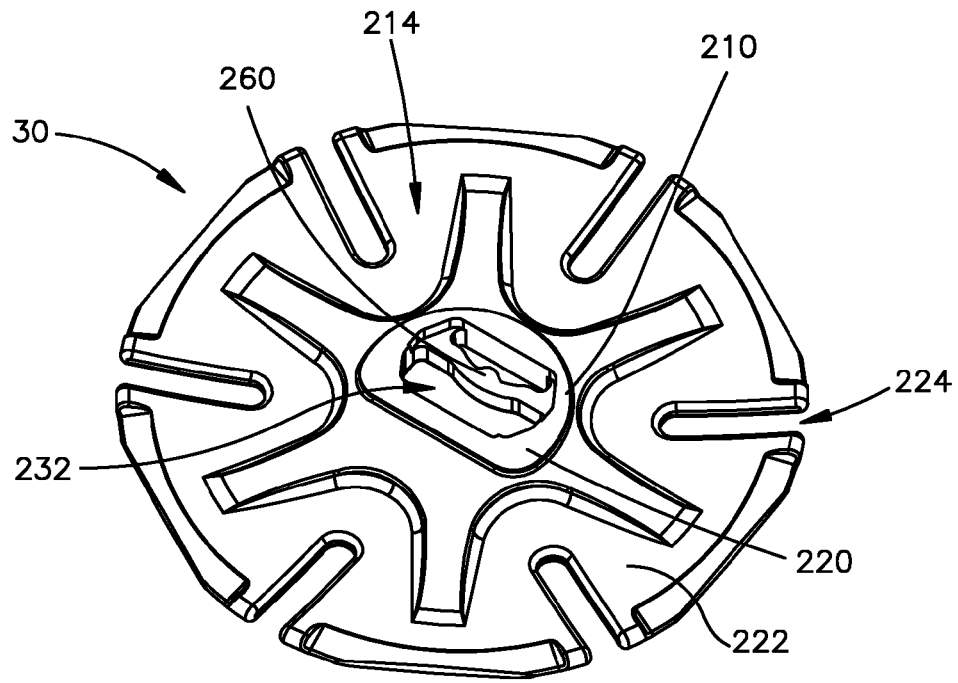
FIG. 5A is a bottom perspective view of the second clamp member shown in FIG. 2A, the second clamp member defining a second stem receiving slot, and including at least one tooth that extends from a surface that defines the second stem receiving slot, and further including a biasing member that extends into the second stem receiving slot and defines an abutment surfaces that faces the at least one tooth such that as the toothed member is received in the second stem receiving slot, the biasing member biases the toothed stem toward the at least one tooth.
Figure 5B:
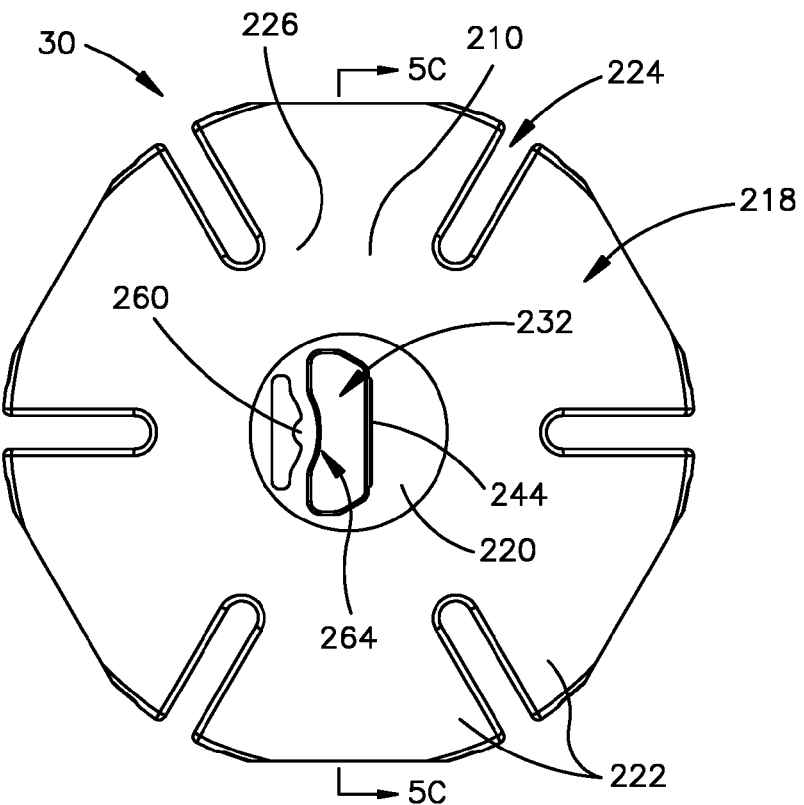
FIG. 5B is a top plan view of the second clamp member shown in FIG. 5A.
Figure 5C:
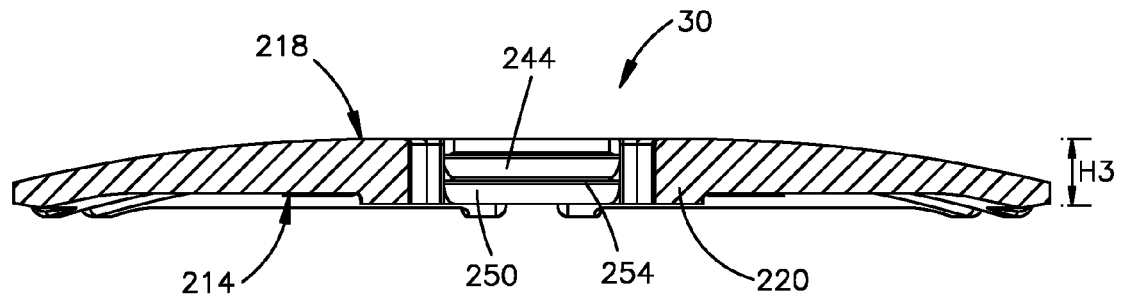
FIG. 5C is a cross-sectional view of the second clamp member shown in FIG. 5B through the line 5C-5C.

Now in reference to FIGS. 5A-5E, the second clamp member 30 is configured to be slidable along the stem body 50 from the proximal stem end P toward the first clamp member 26. The second clamp member 30 includes a second clamp or locking body 210 that is substantially cylindrical in shape when viewed from above and defines an inner or bone contacting surface 214 and an outer surface 218 that is opposite the inner surface 214 along the transverse direction T. As shown in FIGS. 5A and 5B, the second body 210 includes a central core 220 and a plurality of flexible extensions 222 that extend radially out from the core 220. Each flexible extension 222 is separated from an adjacent flexible extension 222 by a radial slot 224. As shown in FIG. 5C, the outer surface 218 which includes the outer surface of the core 220 and of the flexible extensions 222 can be substantially convex.

Each flexible extension 222 is coupled to the core 220 by a respective hinge 226. When the inner surface 214 is brought into contact with the outer surfaces 44*a* and 44*b* of the first and second anatomical structures 16*a* and 16*b* the flexible extensions 222 flex outwardly about their respective hinges 226. In the illustrated embodiment, each flexible extension 222 is trapezoidal in shape though it should be appreciated that the flexible extensions 222 can have any shape as desired. Moreover, it should be appreciated that the second body 210 can have any configuration as desired. For example, the second body 210 can be rectangular shaped and/or the inner and outer surfaces 214 and 218 can be substantially flat.

As shown in FIGS. 5A-5D the second clamp member 30 further defines a second stem receiving slot 232 that extends through the second body 210 from the inner surface 214 through to the outer surface 218 along the transverse direction T. The second stem receiving slot 232 is shaped to receive the stem body 50 along the insertion direction I such that the inner surface 214 faces the distal stem end P or the first clamp member 26 as the second clamp member 30 is being slid along the stem body 50 from the proximal stem end P toward the first clamp member 26. The second stem receiving slot 232 is configured to receive the proximal stem end P of the toothed stem 22 such that the stem body 50 is configured to translate through the second stem receiving slot 232 uni-directionally along the insertion direction I. Therefore, the stem body 50 can translate through the second stem receiving slot 232 along the insertion direction I, but not along a direction opposite the insertion direction.

In cross-section the second stem receiving slot 232 is trapezoidal in shape and corresponds to the trapezoidal shape of the stem body 50. Therefore, the second stem receiving slot 232 will be able to receive the stem body 50 only when the stem body 50 is in the correct orientation. It should be appreciated, however, that the second stem receiving slot 232 can have any configuration as desired. For example, the second stem receiving slot 232 can be rectangular shaped in cross-section similar to that of the first stem receiving slot 122 of the first clamp member 26.

Figure 5D:
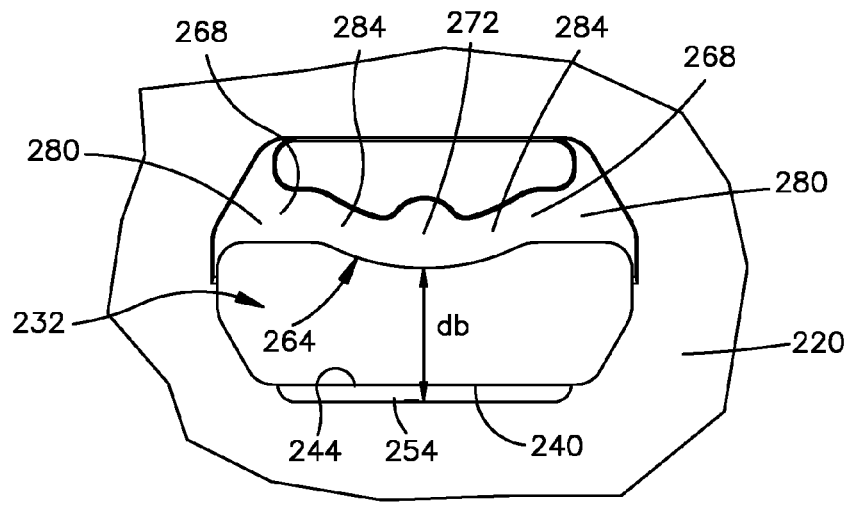
FIG. 5D is an enhanced top view of the biasing member of the second clamp member shown in FIG. 5B in a first or initial position.

As shown in FIGS. 5C and 5D, the second stem receiving slot 232 is partially defined by an internal or slot surface 240 that extends from the inner surface 214 through to the outer surface 218 and the second clamp member 30 includes at least one locking tooth 244 such as two locking teeth 244 that extend out from the internal surface 240 and into the second stem receiving slot 232. Therefore, it can be said that the at least one locking tooth 244 at least partially defines the second stem receiving slot 232. Each locking tooth 244 defines a beveled leading edge 250 that is configured to cam over the complementary beveled leading edge 80 of the locking teeth 76 when the stem body 50 is translated through the second stem receiving slot 232 along the insertion direction I. Each locking tooth 244 further defines a trailing edge 254 that is sloped less than the beveled leading edge 250 such that the trailing edges 254 engage the trailing edges 84 of the locking teeth 76 to prevent the stem body 50 from translating through the second stem receiving slot 232 along a direction opposite the insertion direction I.

Referring to FIG. 5C, the fixation device 14 can include a biasing member 260 that biases the toothed locking stem 22 toward the locking teeth 76. In the illustrated embodiment, the second clamp member 30 includes the biasing member 260 and the biasing member 260 extends into the second stem receiving slot 232 and faces the slot surface 240. In particular, the biasing member 260 defines a curved biasing or abutment surface 264 that is opposed to and faces the at least one locking tooth 244 of the second clamp member 30. As shown in FIG. 5C, the biasing member 260 includes first and second legs 268 that are joined by an abutment member 272. The first and second legs 268 extend from opposed slot surfaces 276 that at least partially define the second stem receiving slot 232. The slot surfaces 276 extend from opposite ends of the slot surface 240 and face each other in the longitudinal direction L. Each leg 268 includes a straight section 280 that is substantially parallel to the slot surface 240 and a curved section 284 that curves toward the slot surface 240. The curved sections 284 are joined at the abutment member 272 such that the abutment member 272 defines the abutment surface 264. As shown in FIG. 5C, the abutment surface 264 is opposed to and faces the at least one locking tooth 244. It should be appreciated, however, that the biasing member 260 can have any configuration as desired.

Figure 5E:
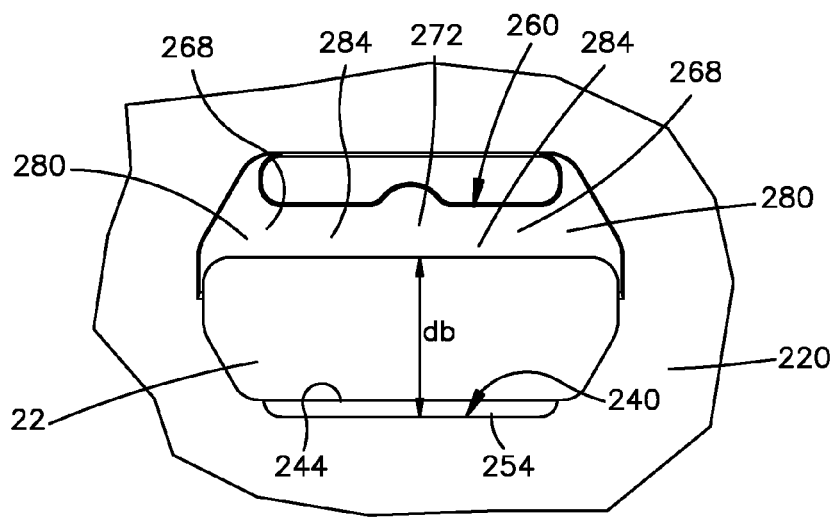
FIG. 5E is an enhanced top view of the biasing member of the second clamp member shown in FIG. 5D in a second or flexed position after the slot has received the toothed stem.

As shown in FIGS. 5D and 5E, the biasing member 260 is flexible between a first or initial position and a second or flexed position. The biasing member 260 has a flexibility that is greater than that of the internal surface 240. When in the first position, the second clamp member 30 defines a member distance $d_b$ measured between the biasing member 260 and the internal surface 240 along the lateral direction A that is less than the maximum distance $d_M$ of the toothed stem 22. When the slot 232 receives the toothed stem 22, the biasing member 260 flexes to the second position whereby the member distance $d_b$ is substantially equal to the maximum distance $d_M$. As a result, the biasing member 260 biases the toothed stem 22 toward the internal surface 240 so as to interlock at least one of the plurality of teeth 76 with the at least one tooth 244.

With continued reference to FIGS. 5D and 5E, it can also be said that the member distance $d_b$ is measured from the abutment surface 264 to the slot surface 240 measured along the lateral direction A is less than the maximum distance $d_M$ of the stem body 50 measured along the lateral direction A when the biasing member 260 is in the first position. Therefore, when the stem body 50 is inserted through the second stem receiving slot 232, the biasing member 260 will flex to the second position to thereby widen the member distance $d_b$ so that the stem body 50 can pass through the second stem receiving slot 232. The biasing member 260 will as a result bias or otherwise apply a force F against the second surface 50b of the stem body 50 to thereby force the stem body 50 toward the slot surface 240. The biasing member 260 can be configured to apply a biasing force F that is between about 05 N and about 100 N and in particular between about 10 N and about 30 N. In the illustrated embodiment, the biasing member 260 applies a biasing force F of about 30 N. It should be appreciated, however, that the biasing member 260 can be configured to apply any biasing force F as desired.

As shown in FIG. 5C, the second clamp member 30 is configured to have only two locking teeth 244 and therefore can have a lower profile as compared to locking members that have three or more locking teeth. In particular, the second clamp member 30 is configured to have a height $H_3$ that is measured along the transverse direction T that is between about 1.0 mm and about 2.0 mm. For example, in the illustrated embodiment, the second clamp member 30 has a height $H_3$ that is about 1.25 mm. It should be appreciated, however, that the second clamp member 30 can have any height $H_3$ as desired.

The second clamp member 30 is configured to be positioned over the proximal stem end P such that the proximal stem end P is inserted through the second stem receiving slot 232 along the insertion direction I from the inner surface 214 to the outer surface 218. The second clamp member 30 can then be slid along the stem body 50 toward the first clamp member 26. The second clamp member 30 can be slid along the stem body until the second clamp member 30 abuts or otherwise contacts the outer surfaces 44a and 44b of the first and second anatomical structures 16a and 16b. As the second clamp member 30 is slid along the stem body 50, the locking teeth 76 of the toothed stem 22 will engage the locking teeth 244 of the second clamp member 30. The engagement between the locking teeth 244 and the locking teeth 76 will prevent the second clamp member 30 from moving along the stem body 50 away from the first clamp member. In this way, the second clamp member 30 can also be referred to as a second locking member.

It should be appreciated that the second locking member or at least some of the features of the second locking member can be incorporated into other bone fixation devices. For example, the second locking member can be incorporated into a bone fixation member such as a sternal tie having a flexible strap configured to be formed into a loop around first and second boney structures. In such an embodiment, the slot of the second locking member can be configured to receive the flexible strap such that the biasing member applies a force against the flexible strap so as to cause locking teeth of the flexible strap to engage the locking teeth of the second locking member. For example, the second locking head can be incorporated into any one of the locking members disclosed in United States Provisional Application No. 61/616,555 filed Mar. 28, 2012, the disclosure of which is hereby incorporated by reference herein.

Referring to FIGS. 6A-6D, in operation the first locking member can be positioned such that the first clamp member 26 is proximate to the inner surfaces 40a and 40b of the first and second anatomical structures 16a and 16b and the toothed stem 22 extends through the bone gap 18 such that a portion of the toothed stem 22 is external to the anatomical structures 16a and 16b. Once the first locking member is in position, the second locking member (i.e. the second clamp member 30) can be positioned such that the stem body 50 is inserted through the second stem receiving slot 232 along the insertion direction I such that the biasing member 260 biases the stem body 50 toward the locking teeth 244. The second clamp member 30 can then be slid or otherwise translated along the stem body 50 toward the first clamp member 26 such that at least one tooth of the toothed stem 22 engages the at least one tooth 244 of the second clamp member 30 to thereby prevent the second clamp member from translating along the toothed stem 22 away from the first clamp member 26. As shown in FIG. 6C, the second clamp member 30 can be slid along the stem body 50 until the first and second clamp member 26 and 30 have abutted the inner surfaces 40a and 40b and outer surfaces 44a and 44b of the first and second anatomical structures 16a and 16b respectively, such that the first and second anatomical structures are sandwiched or otherwise trapped between the first and second clamp members 26 and 30. This process can be repeated as many times as desired. Therefore, the first anatomical structure 16a can be affixed relative to the second anatomical structure 16b with one bone fixation device 14 or any number of bone fixation devices 14 as desired.

In another embodiment and in reference to FIGS. 7A and 7B, the fixation device 14 can be configured such that the biasing member extends from a toothed stem 322. In such an embodiment, the biasing member will press against a second slot surface that is opposite the slot surface 240 to thereby bias locking teeth of the toothed stem toward the locking teeth 244. As shown in FIG. 7A, the toothed stem 322 can include a stem body 350 that is separated into at least a first initiation region 354 that extends from the proximal stem end P toward the distal stem end D along a portion of the length of the toothed stem 322 (for instance, approximately ½ the length of the stem 22) and a second locking region 358 that extends between the first initiation region 354 and the distal stem end D. In accordance with the illustrated embodiment, the second locking region 358 extends from the first initiation region 354 to a location that is spaced from the distal stem D. The stem body 350 defines opposed first and second surfaces 350a and 350b that are spaced from each other along the lateral direction A. As shown, the first and second surfaces 350a and 350b are connected together by a pair of side surfaces 351a and 351b. As shown, the first and second surfaces 350a and 350b are wider than the side surfaces 351a and 351b. It should be appreciated, however, that the first and second surfaces 350a and 350b can be narrower than the side surfaces 351a and 351b, as desired.

As shown in FIGS. 7A and 7B, the second locking region 358 of the toothed stem 322 can include a plurality of locking teeth 376 that extend out from the first surface 350a of the stem body 350 a distance greater than that of the protrusions and are separated by recessed regions 378 that are disposed between adjacent locking teeth 376. It should be appreciated that the locking region 358 can extend along any portion up to all of the stem body 350, as desired.

The locking teeth 376 extend from the stem body 350 along only the first surface 350a and are spaced from each other along the transverse direction T. Each locking tooth 376 is elongate along the longitudinal direction and is spaced from an adjacent tooth along the transverse direction T. Each tooth 376 is similar to the locking teeth 76 and defines a beveled leading or proximal edge and a trailing or distal edge. The leading edges extend from the first surface 350a at an angle such that the leading edges are configured to cam over complementary beveled leading edges of complementary locking teeth of the second clamp member 30. The trailing edges extend from the first surface 350a along the lateral direction and are substantially perpendicular to the first surface 350a such that the trailing edges are configured to engage complementary trailing edges of the locking teeth of the second clamp member 30. It should be appreciated, however, that the locking teeth 376 can have other configurations as desired.

As shown in FIG. 7B, the bone fixation device can include a biasing member 380 that extends from the second surface 350b. The biasing member 380 includes at least one such as a pair of flexible fingers 384 that extend out from the second surface 350b such that the fingers 384 are spaced from each other along the longitudinal direction. Each finger 384 extends at least partially toward the other such that an inner surface 392 of each finger 384 faces and is spaced from the second surface 350b. The fingers 384 extend along at least a portion such as the entire second locking region 358 of the stem body 350. Therefore, when the stem body 350 is translating through the second stem receiving slot 232 along the insertion direction I, the biasing member 380 will bias the stem body 350 toward the locking teeth 244.

Figure 8B:
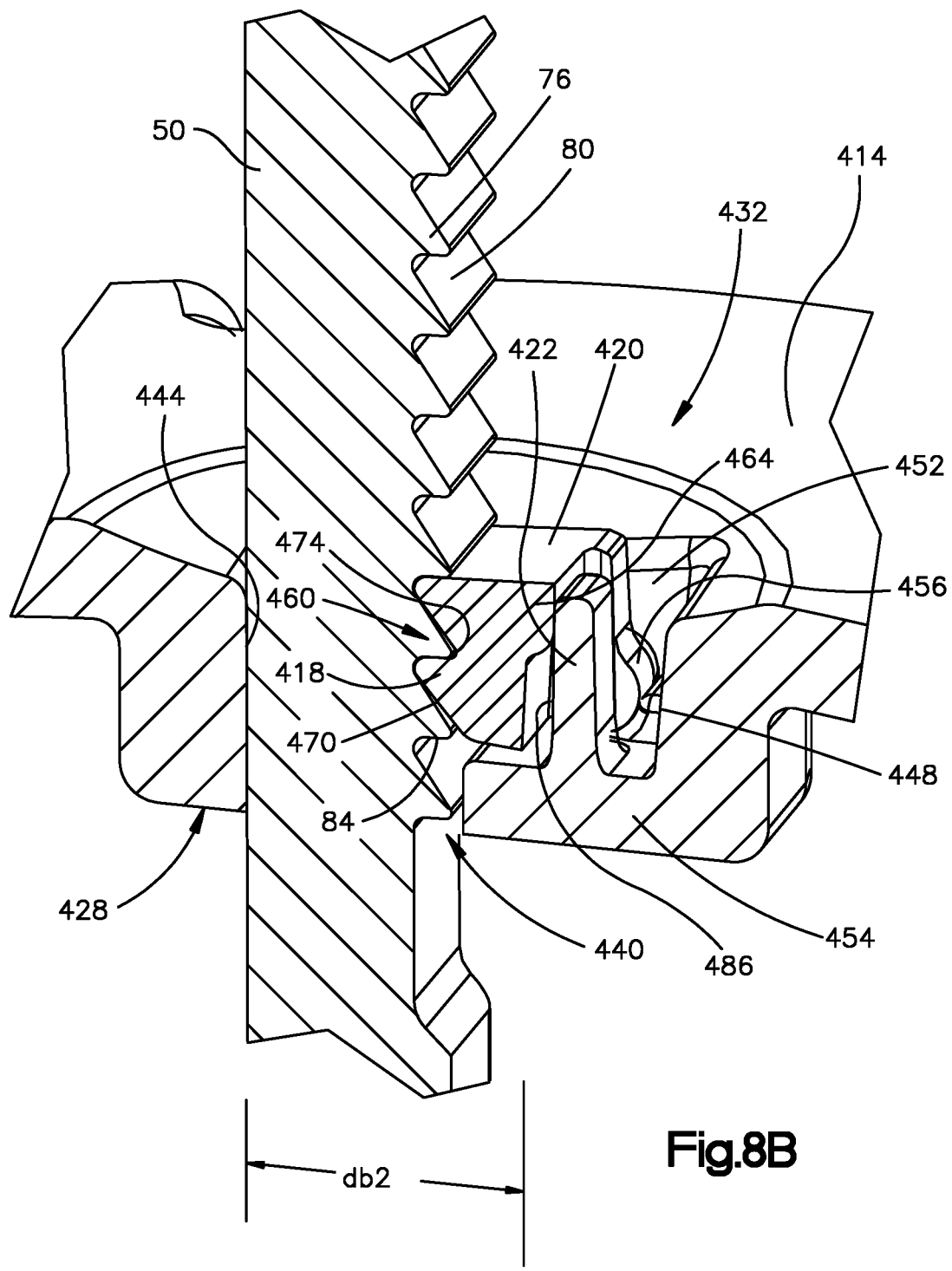
FIG. 8B is a detailed cross-sectional view of the toothed body and biasing member of the locking body shown in FIG. 8A.

Now in reference to FIGS. 8A and 8B, the clamp member can be a locking member 410 that is configured to include a locking body 414, at least one tooth such as two teeth 418 configured as a toothed body 420 that is rotatably coupled to the locking body 414, and a biasing member 422 that extends from the locking body 414 and is configured to bias the toothed body 420. As with the biasing member 260, the biasing member 422 is separate from the toothed body 420 and therefore is void of any locking teeth. The biasing member 422 is configured to apply a biasing force to the toothed body 420 so as to cause the toothed body 420 to rotate or otherwise pivot toward the toothed member.

As shown in FIG. 8A, the locking member 410 is similar to the second clamp member 30 and includes like structure unless otherwise stated. For example, the locking member 410 is configured to be slidable along the stem body 50 from the proximal stem end P toward the distal end D such as toward a first clamp member. The locking body 414 is substantially cylindrical in shape when viewed from above and defines an inner or bone contacting surface 428 and an outer surface 432 that is opposite the inner surface 428 along the transverse direction T.

As shown in FIGS. 8A and 8B, the locking member 410 further defines a second stem receiving slot 440 that extends through the locking body 414 from the inner surface 428 through to the outer surface 432 along the transverse direction T. The second stem receiving slot 440 is shaped to receive the stem body 50 along the insertion direction I such that the inner surface 428 faces the distal stem end P or the first clamp member as the locking member 410 is being slid along the stem body 50 from the proximal stem end P toward the first clamp member. The second stem receiving slot 440 is configured to receive the proximal stem end P of the toothed stem 22 such that the stem body 50 is configured to translate through the second stem receiving slot 440 unidirectionally along the insertion direction I. Therefore, the stem body 50 can translate through the second stem receiving slot 440 along the insertion direction I, but not along a direction opposite the insertion direction.

As shown in FIG. 8B, the second stem receiving slot 440 is partially defined by a first slot or internal surface 444 that extends from the inner surface 428 through to the outer surface 432, a second internal surface 448 that is opposed to the first internal surface 444, and a pair of side surfaces 452 that are opposed to each other and extend from the first internal surface 444 to the second internal surface 448. The locking body 414 further includes a platform 454 that extends out from at least one of the side surfaces 452 and second internal surface 448 and toward the first internal surface 444.

The toothed body 420 is movably coupled to at least one of the side surfaces 452. In the illustrated embodiment the toothed body 420 is rotatably coupled to at least one of the side surface 452 at a pivot 456. The toothed body 420 defines an engagement side 460 and an opposed biasing side 464. The engagement side 460 defines the locking teeth 418 such that the locking teeth 418 face the first internal surface 444. Each locking tooth 418 defines a beveled leading edge 470 that is configured to cam over the complementary beveled leading edge 80 of the locking teeth 76 when the stem body 50 is translated through the second stem receiving slot 440 along the insertion direction I. Each locking tooth 418 further defines a trailing edge 474 that is sloped less than the beveled leading edge 470 such that the trailing edges 474 engage the trailing edges 84 of the locking teeth 76 to prevent the stem body 50 from translating through the second stem receiving slot 440 along a direction opposite the insertion direction I.

The biasing member 422 extends up from the platform 454 such that the biasing member 422 is spaced from the second internal surface 448. The biasing member 422 defines a biasing surface 486 that abuts the biasing side 464 of the toothed body 420 so as bias the toothed body 420 toward the first internal surface 444. As shown, the biasing surface 486 is spaced from the pivot 456 along the insertion direction I. In the illustrated embodiment, the pivot 456 is disposed proximate to the inner bone contacting surface 428 and the biasing surface 486 abuts the biasing side 464 proximate to the outer surface 432. It should be appreciated, however, that the pivot 456 and the biasing surface 486 can be disposed anywhere along the insertion direction I within the slot 440. For example, the pivot 456 can be disposed proximate to the outer surface 432 and the biasing surface can be disposed proximate to the inner surface 428. When the stem body 50 translates through the slot 440, the stem body 50 will be biased against the internal surface 444 by the biasing member 422.

As shown in FIG. 8B, the biasing member 422 is flexible between a first or initial position and a second or flexed position. The biasing member 422 has a flexibility that is greater than that of the internal surface 444. When in the first position, the locking member 410 defines a member distance $d_{b2}$ measured between the biasing member 422 and the internal surface 444 along the lateral direction A. When the slot 440 receives the stem body 50, the biasing member 422 flexes to the second position whereby the member distance $d_{b2}$ increases. As a result, the biasing member 422 biases the toothed stem 22 toward the internal surface 444 so as to interlock at least one of the plurality of teeth 76 with the at least one tooth 418.

For example, when the stem body 50 is inserted through the second stem receiving slot 440, the biasing member 422 will flex to the second position to thereby widen the member distance $d_b$ so that the stem body 50 can pass through the second stem receiving slot 440. The biasing member 422 will as a result bias or otherwise apply a force F against the biasing side 464 of the toothed body 420 so as to cause the toothed body 420 to rotate about the pivot 456 and force the stem body 50 toward the slot surface 444. Engagement of the at least one tooth 418 with the teeth 76 of the stem body 50 will prevent the stem body 50 from translating through the slot 440 along a direction opposite the insertion direction I. It should be appreciated that the locking member 410 can be configured to receive any toothed member and is not limited to stem bodies 50.

The bone fixation assembly 10 can include any number of bone fixation devices 14. Additionally, the bone fixation assembly 10 can include an implant that is to be affixed to the surrounding skull 16b by the bone fixation devices 14. Therefore the bone fixation assembly 10 can be a kit that includes an implant and a plurality of bone fixation devices 14. Further the bone fixation devices 14 can include any of the locking members and toothed members described.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

What is claimed:

1. A bone fixation device comprising:
    a stem that is elongate along a first direction and includes a first end and a second end that is spaced from the first end along the first direction, the stem further including at least one first tooth;
    a first fixation member fixed to the first end of the stem with respect to translation relative to the stem along the first direction; and
    a second fixation member including a body that defines an inner surface and an outer surface opposite the inner surface, the second fixation member including an internal surface that at least partially defines a slot that extends through the body from the inner surface to the outer surface, the slot being sized to receive the stem such that the second fixation member is slidable along the stem along the first direction, the second fixation member further including at least one second tooth that extends from the internal surface; and a biasing member having a flexibility greater than that of the internal surface, the biasing member configured to bias the stem toward the at least one second tooth when the stem extends through the slot such that the at least one first tooth engages the at least one second tooth so as to i) permit the at least one second tooth to slide along the at least one first tooth when the second fixation member translates along the stem toward the first fixation member, and ii) cause the at least one second tooth to interlock with the at least one first tooth to prevent the second fixation member from translating along the stem away from the first fixation member.

2. The bone fixation device of claim 1, wherein the biasing member extends from the body into the slot and faces the at least one second tooth.

3. The bone fixation device of claim 2, wherein the biasing member defines a curved abutment surface that faces the at least one second tooth of the second fixation member.

4. The bone fixation device of claim 3, wherein the biasing member includes first and second curved legs that are joined by an abutment member that defines the abutment surface, the first and second legs extending from opposed surfaces that at least partially define the slot.

5. The bone fixation device of claim 4, wherein the abutment member has a thickness measured along a direction that is perpendicular to the first direction that is greater than that of the first and second legs.

6. The bone fixation device of claim 2, wherein the stem has first and second surfaces that are opposed along a second direction that is perpendicular to the first direction, and wherein the stem includes a plurality of teeth that extend only from the first surface and the biasing member is configured to apply a force against the second surface when the stem is inserted through the slot along the first direction.

7. The bone fixation device of claim 6, wherein the stem further includes a first coupling member at the first end and a pair of second coupling members that extend from the first and second surfaces respectively at a location spaced from the first coupling member such that first and second gaps are defined between the first coupling member and the second coupling members respectively, and wherein the first and second gaps receive a portion of the first fixation member to thereby couple the first fixation member to the stem.

8. The bone fixation device of claim 7, wherein the first fixation member defines a recess that extends into a first outer surface of the first fixation member, the recess being configured to receive the first coupling member when the first fixation member is coupled to the stem.

9. The bone fixation device of claim 1, wherein the second fixation member includes a plurality of flexible extensions that are configured to flex when the second fixation member is moved along the stem toward the first fixation member and the second fixation member abuts outer surfaces of respective anatomical structures.

10. The bone fixation device of claim 1, wherein the second fixation member includes two teeth that extend from the body and into the slot.

11. The bone fixation device of claim 1, wherein the second fixation member has a maximum height measured along the first direction that is between about 1 mm and about 2 mm.

12. The bone fixation device of claim 1, wherein the biasing member is configured to apply a force to the stem that is between about 10 N and about 30 N.

13. The bone fixation device of claim 1, wherein the stem has first and second surfaces that are opposed along a second direction that is perpendicular to the first direction, and wherein the stem includes a plurality of teeth that extend only from the first surface and the biasing member extends out from the second surface.

14. The bone fixation device of claim 13, wherein the biasing member includes a pair of flexible fingers that extend out from the second surface such that the fingers are spaced from each other and extend toward each other.

15. The bone fixation device of claim 14, wherein each finger defines an inner surface that faces the second surface.

16. The bone fixation device of claim 14, wherein the stem includes a plurality of teeth that are spaced from each other along the first direction such that the portion of the stem that includes the teeth defines a locking region and wherein the biasing member extends along the entire locking region.

17. A locking member for a bone fixation device, the locking member comprising:

a locking body that defines an outer surface, an inner bone contacting surface opposite the outer surface along a first direction, an internal surface that extends between the inner bone contacting surface and the outer surface, and at least one locking tooth that extends from the internal surface;

a biasing member that is supported by the locking body and configured to flex along a second direction substantially perpendicular to the first direction, the biasing member defining a biasing surface that faces the internal surface, wherein the locking body is configured to receive a toothed member such that the biasing surface abuts the toothed member to thereby bias the toothed member toward the at least one locking tooth so as to i) permit the toothed member to translate through the locking body along a direction that extends from the inner surface to the outer surface, and ii) prevent the toothed member from translating through the locking body along a direction that extends from the outer surface to the inner surface.

18. The locking member of claim 17 wherein the internal surface at least partially defines a slot that extends from the inner bone contacting surface to the outer surface.

19. The locking member of claim 18, wherein the slot is a stem receiving slot configured to receive a stem that has first and second opposed surfaces, and wherein the stem includes a plurality of teeth that extend only from the first surface and the biasing member is configured to apply a force against the second surface when the stem is inserted through the slot.

20. The locking member of claim 17, wherein the biasing surface is a curved abutment surface.

21. The locking member of claim 20, wherein the biasing member includes first and second curved legs that are joined by an abutment member that defines the abutment surface, the first and second legs extending from opposed surfaces that at least partially define the slot.

22. The locking member of claim 17, wherein the abutment member is configured to apply a force to the toothed member that is between about 10 N and about 30 N.

23. The locking member of claim 17, wherein the locking body includes a plurality of flexible extensions that are configured to flex.

24. The locking member of claim 18, wherein two locking teeth extend from the internal surface and into the slot.

25. The locking member of claim 17, wherein the locking body has a maximum thickness measured along a direction from the outer surface to the inner surface that is between about 1 mm and about 2 mm.

26. The locking member of claim 17, wherein the locking body defines a slot that has a trapezoidal shape in cross-section, the slot being configured to receive the toothed member.

27. A bone fixation device comprising:
- a stem including a first end and a second end that is spaced from the first end along a first direction, the stem further including a stem body and a plurality of teeth that extend out from the stem body and are spaced from each other along the first direction, the stem defining a maximum width from an exterior surface of the stem body to an outermost surface of at least one of the plurality of teeth along a second direction that is substantially perpendicular to the first direction;
- a first member coupled to the stem proximate to the first end; and
- a second member including a member body, the second member including:
  - a slot that extends through the member body along the first direction, the slot being defined by at least one internal surface of the member body;
  - at least one tooth that extends from the at least one internal surface and into the slot; and
  - a biasing member that extends from the member body and into the slot, the second member defining a member distance between the biasing member and the internal surface along the second direction, wherein the biasing member is flexible between a first position and a second position, such that when in the first position the member distance is less than the maximum width,
- wherein the slot is configured to receive the stem such that the stem causes the biasing member to flex from the first position to the second position whereby the member distance is substantially equal to the maximum width, such that the biasing member biases the stem toward the internal surface so as to interlock at least one of the plurality of teeth with the at least one tooth.

28. The bone fixation device of claim 27, wherein the biasing member biases the stem toward the internal surface so as to i) permit the second member to translate along the stem toward the first member, and ii) prevent the second member from translating along the stem away from the first member.

29. The bone fixation device of claim 28, wherein the biasing member is resiliently biased toward the first position.

30. The locking member of claim 29, wherein the member body has a maximum thickness measured along the first direction that is between about 1 mm and about 2 mm.

31. The locking member of claim 27, wherein the biasing member is configured to apply a force to the stem that is between about 10 N and about 30 N.

32. A method of affixing a first anatomical structure to a surrounding skull portion, the method comprising:
- positioning a locking member such that (i) a first clamp member of the locking member is proximate to respective inner surfaces of the first anatomical structure and the surrounding skull portion and (ii) a toothed stem of the locking member that extends from the first clamp member along a first direction protrudes out from between the first anatomical structure and the surrounding skull portion such that a portion of the toothed stem is external to the surrounding skull portion;
- inserting the toothed stem through a stem receiving slot of a second clamp member such that a biasing member of the second clamp member that extends into the stem receiving slot biases the toothed stem toward at least one tooth of the second clamp member that extends into the stem receiving slot; and
- translating the second clamp member along the toothed stem and toward the first clamp member such that at least one tooth of the toothed stem engages the at least one tooth of the second clamp member to thereby prevent the second clamp member from translating along the toothed stem away from the first clamp member.

33. The method of claim 32, wherein the step of translating the second clamp member comprises moving the second clamp member so that a bone contacting surface of the second clamp member abuts respective outer surfaces of the first anatomical structure and the surrounding skull portion.

34. The method of claim 32, wherein the translating step further comprises moving the second clamp member so that the bone contacting surface of the second clamp member abuts respective outer surfaces of the first anatomical structure and the surrounding skull thereby causing flexible extension of the second clamp member to flex.

* * * * *